United States Patent [19]
Castro Pineiro et al.

[11] Patent Number: 5,977,116
[45] Date of Patent: Nov. 2, 1999

[54] PIPERAZINE, PIPERIDINE AND TETRAHYDROPYRIDINE DERIVATIVES

[75] Inventors: Jose Luis Castro Pineiro; Angus Murray MacLeod, both of Bishops Stortford; Michael Rowley, Harlow; Monique Bodil Van Niel, Welwyn Garden City, all of United Kingdom

[73] Assignee: Merck Sharp & Dohme Ltd., Hoddesdon, United Kingdom

[21] Appl. No.: 09/068,680

[22] PCT Filed: Nov. 13, 1996

[86] PCT No.: PCT/GB96/02762

§ 371 Date: May 12, 1998

§ 102(e) Date: May 12, 1998

[87] PCT Pub. No.: WO97/18203

PCT Pub. Date: May 22, 1997

[30] Foreign Application Priority Data

Nov. 14, 1995 [GB] United Kingdom ............... 9523250

[51] Int. Cl.⁶ ............... A01N 43/60; C07D 401/00; C07D 403/00; C07D 413/00
[52] U.S. Cl. ............... 514/255; 544/362; 544/366; 544/367; 544/369; 544/370; 544/371; 544/372; 544/373; 514/253
[58] Field of Search ............... 544/362, 372, 544/373, 368, 371, 366, 367, 369, 370; 514/253, 255

[56] References Cited

U.S. PATENT DOCUMENTS 5,854,247  12/1998  Baker et al. ............... 514/253

FOREIGN PATENT DOCUMENTS

94/02477  3/1994  WIPO .
95/32196  3/1995  WIPO .
96/16056  5/1996  WIPO .

*Primary Examiner*—Alan L. Rotman
*Assistant Examiner*—Rita Desai
*Attorney, Agent, or Firm*—James L. McGinnis; David L. Rose

[57] ABSTRACT

A class of N-substituted piperazine, piperidine and tetrahydropyridine derivatives, linked by a fluoro-substituted alkylene chain to a fused bicyclic heteroaromatic moiety such as indolyl, and further substituted at the 4-position by an optionally substituted alkenyl, alkynyl, aryl-alkyl or heteroaryl-alkyl moiety, are selective agonists of $5\text{-}HT_1$-like receptors, being potent agonists of the human $5\text{-}HT_{1D\alpha}$ receptor subtype whilst possessing at least a 10-fold selective affinity for the $5\text{-}HT_{1D\alpha}$ receptor subtype relative to the $5\text{-}HT_{1D\beta}$ subtype; they are therefore useful in the treatment and/or prevention of clinical conditions, in particular migraine and associated disorders, for which a subtype-selective agonist of $5\text{-}HT_{1D}$ receptors is indicated, whilst eliciting fewer side-effects, notably adverse cardiovascular events, than those associated with non-subtype-selective $5\text{-}HT_{1D}$ recptor agonists.

10 Claims, No Drawings

PIPERAZINE, PIPERIDINE AND TETRAHYDROPYRIDINE DERIVATIVES

CROSS-REFERENCE

This application is a 371 of PCT/GB96/02762 filed May 12, 1998.

The present invention relates to a class of substituted piperazine, piperidine and tetrahydropyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the piperazine, piperidine and tetrahydropyridine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an optionally substituted alkenyl, alkynyl, aryl-alkyl or heteroaryl-alkyl substituent; nor is there any suggestion therein that the alkylene chain present in the indol-3-ylalkylpiperazine portion of the molecule might be substituted with one or more fluorine atoms.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the piperazine, piperidine and tetrahydropyridine derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

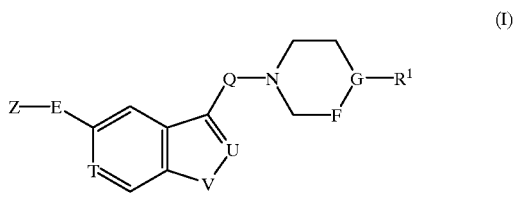

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR⁵R⁶, or a group of formula (Za), (Zb), (Zc) or (Zd):

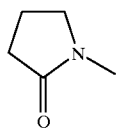
(Za)

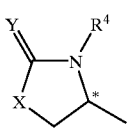
(Zb)

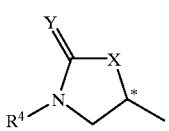
(Zc)

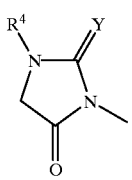
(Zd)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, substituted in any position by one or more fluorine atoms;

T represents nitrogen or CH;

U represents nitrogen or C—R²;

V represents oxygen, sulphur or N—R³;

—F—G— represents —CH₂—N—, —CH₂—CH— or —CH=C—;

R¹ represents $C_{3-6}$ alkenyl, $C_{3-6}$ alkynyl, aryl($C_{1-6}$)alkyl or heteroaryl($C_{1-6}$)alkyl, any of which groups may be optionally substituted;

R², R³ and R⁴ independently represent hydrogen or $C_{1-6}$ alkyl; and

R⁵ and R⁶ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or R⁵ and R⁶, when linked through a nitrogen atom, together represent the residue of an optionally substituted azetidine, pyrrolidine, piperidine, morpholine or piperazine ring.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group R¹ may be optionally substituted by one or more substituents, as also may the groups R⁵ or R⁶ where these represent aryl($C_{1-6}$)alkyl or heteroaryl($C_{1-6}$)alkyl. Where R¹, R⁵ or R⁶ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$)alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, aminosulphonylmethyl, $C_{1-6}$ alkylaminosulphonylmethyl and di($C_{1-6}$)alkylaminosulphonylmethyl.

When R⁵ and R⁶, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where R⁵ and R⁶ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolvl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furyimethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridinylpropyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. For example, the compounds of formula I above wherein Z represents a group of formula (Zb) or (Zc) have a chiral center denoted by the asterisk *, which may accordingly be in the (R) or (S) configuration. It is to be understood that all such isomers and mixtures thereof in any proportion are encompassed within the scope of the present invention.

The alkylene chain E may be, for example, methylene, ethylene, 1-methylethylene, propylene, 2-methylpropylene or butylene. In addition, E may represent a chemical bond such that the moiety Z is attached directly to the central fused bicyclic heteroaromatic ring system containing the variables T, U and V.

Suitably, E represents a chemical bond or a methylene linkage.

The alkylene chain Q is substituted in any position by one or more fluorine atoms, preferably by one or two fluorine atoms and more preferably by one fluorine atom. Representative alkylene chains for Q include 2-fluoropropylene, 2,2-difluoropropylene and 2-fluoromethyl-propylene, especially 2-fluoropropylene or 2-fluoromethyl-propylene.

The compound of formula I in accordance with the present invention is suitably an indole, benzofuran or benzthiophene derivative of formula IA, an indazole derivative of formula IB, or a pyrrolo[2,3-c]pyridine derivative of formula IC:

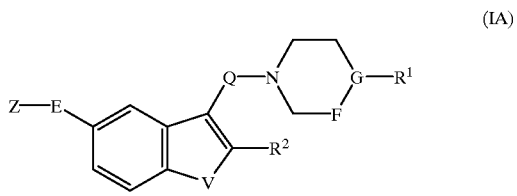

(IA)

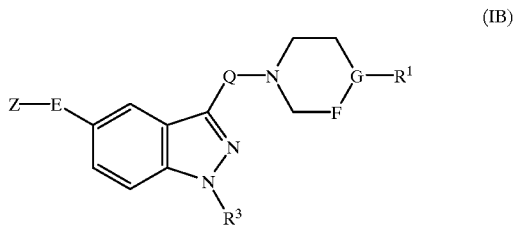

(IB)

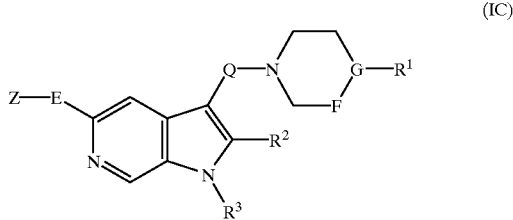

(IC)

wherein Z, E, Q, V, F, G, $R^1$, $R^2$ and $R^3$ are as defined above. Preferably, the compounds according to the invention are indole or pyrrolo[2,3-c]-pyridine derivatives of formula ID:

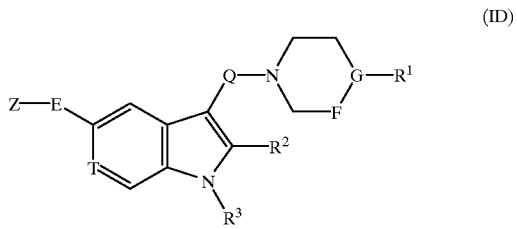

(ID)

wherein Z, E, Q, T, F, G, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, phenylpropyl, furylmethyl, thienylmethyl, thienylethyl, imidazolylmethyl, pyridinylmethyl and pyridinylpropyl, any of which groups may be optionally substituted. Selected values of $R^1$ include allyl, dimethylallyl, butenyl, propargyl, benzyl, phenylethyl, phenylpropyl, furylmethyl, thienylmethyl, imidazolylmethyl and pyridinylmethyl, any of which groups may be optionally substituted. Typical substituents on the group $R^1$ include halogen, cyano, trifluoromethyl, triazolyl, tetrazolyl, $C_{1-6}$ alkyl-tetrazolyl, $C_{1-6}$ alkoxy, amino, di($C_{1-6}$)alkylamino, di($C_{1-6}$) alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Representative values of $R^1$ include allyl, dimethylallyl, butenyl, propargyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl, fluoro-phenylethyl, difluoro-phenylethyl, trifluoromethyl-phenylethyl, cyano-phenylethyl, triazolyl-phenylethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, phenylpropyl, fluoro-phenylpropyl, furylmethyl, thienylmethyl, thienylethyl, imidazolylmethyl, pyridinylmethyl, pyridinylpropyl and amino-pyridylmethyl.

Particular values of $R^1$ include benzyl, phenylethyl, fluoro-phenylethyl, phenylpropyl (especially 2-phenylpropyl), fluoro-phenylpropyl (especially 2-(fluorophenyl)-propyl), thienylethyl, pyridinylmethyl and pyridinylpropyl (especially 2-(pyridinyl)-propyl).

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphehnyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents $-SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral center denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

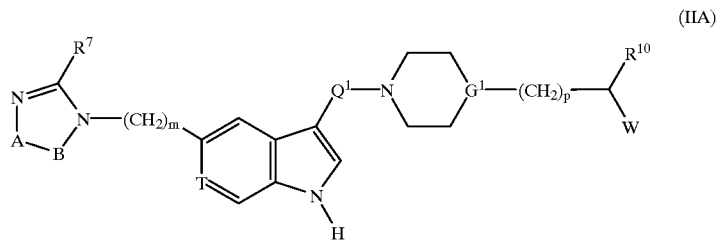

(IIA)

wherein
m is zero, 1, 2 or 3, preferably zero or 1;
p is zero, 1 or 2;
$Q^1$ represents a straight or branched alkylene chain containing from 2 to 5 carbon atoms, substituted in any position by one or more fluorine atoms;
T represents nitrogen or CH;
$G^1$ represents nitrogen or CH;
A represents nitrogen or CH;
B represents nitrogen or $C-R^8$;
$R^7$ and $R^8$ independently represent hydrogen, $C_{1-6}$ alkyl, $C_{2-6}$ alkenyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
W represents a group of formula (Wa), (Wb) or (Wc):

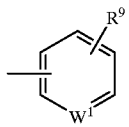

(Wa)

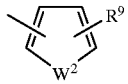

(Wb)

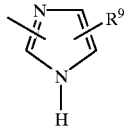

(Wc)

in which
$W^1$ represents CH or nitrogen;
$W^2$ represents oxygen, sulphur, NH or N-methyl;
$R^9$ represents hydrogen, halogen, cyano, trifluoromethyl, triazolyl, tetrazolyl, $C_{1-6}$ alkyltetrazolyl, $C_{1-6}$ alkoxy, $C_{2-6}$ alkylcarbonyl, amino, $C_{1-6}$ alkylamino, di($C_{1-6}$)alkylamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and $R^{10}$ represents hydrogen or $C_{1-3}$ alkyl.

Suitably, $Q^1$ represents a straight or branched 3 or 4 carbon alkylene chain, substituted in any position by one or two fluorine atoms. Where the alkylene linkage $Q^1$ is substituted by two fluorine atoms, the gem difluoro substitution pattern is preferred. Particular alkylene chains for $Q^1$ include 2-fluoropropylene, 2,2-difluoropropylene and 2-(fluoromethyl)-propylene, especially 2-fluoropropylene or 2-(fluoromethyl)-propylene.

Particular values of $R^7$ and $R^8$ include hydrogen, methyl, ethyl, benzyl and amino, especially hydrogen.

Particular values of $R^9$ include hydrogen, fluoro, cyano, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or fluoro.

Particular values of $R^{10}$ include hydrogen and methyl.

Another sub-class of compounds according to the invention is represented by the compounds of formula IIB, and salts and prodrugs thereof:

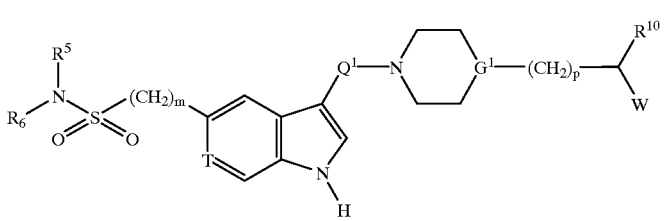

(IIB)

wherein m, p, $Q^1$, T, $G^1$, W and $R^{10}$ are as defined with reference to formula IIA above; and $R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

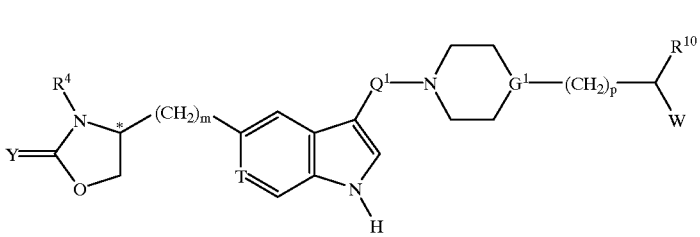

(IIC)

wherein the asterisk * denotes a chiral center;

m, p, $Q^1$, T, $G^1$, W and $R^{10}$ are as defined with reference to formula IIA above; and $R^4$ and Y are as defined with reference to formula I above.

Particular values of $R^4$ in relation to formula IIC include hydrogen and methyl.

Preferably, Y in formula IIC is oxygen.

Preferably, the chiral center denoted by the asterisk * in formula IIC is in the (S) configuration.

Specific compounds within the scope of the present invention include:

4-benzyl-1-[2-fluoromethyl-3-(5-(1,2,4-triazol-4-yl)-1H-indol-3-yl)propyl]piperazine;

4-[2-(3-fluorophenyl)ethyl]-1-[2-fluoro-3-(5-(1,2,4-triazol-4-yl)-1H-indol-3-yl)propyl]piperazine;

4-benzyl-1-[2-fluoro-3-(5-(1,2,4-triazol-4-yl)-1H-indol-3-yl)propyl]piperidine;

4-[2-(2-fluorophenyl)propyl]-1-[2-fluoro-3-(5-(1,2,4-triazol-4-yl)-1H-indol-3-yl)propyl]piperazine;

4-[2-(3-fluorophenyl)propyl]-1-[2-fluoro-3-(5-(1,2,4-triazol-4-yl)-1H-indol-3-yl)propyl]piperazine;

4-[2-(4-fluorophenyl)propyl]-1-[2-fluoro-3-(5-(1,2,4-triazol-4-yl) -1H-indol-3-yl)propyl]piperazine;

4-(2-phenylethyl)-1-[2-fluoro-3-(5-(1,2,4-triazol-4-yl)-1H-indol-3-yl)propyl]piperazine;

4-(2-phenylpropyl)-1-[2-fluoro-3-(5-(1,2,4-triazol-4-yl)-1H-indol-3-yl)propyl]piperazine;

4-[2-(2-fluorophenyl)ethyl]-1-[2-fluoro-3-(5-(1,2,4-triazol-4-yl)-1H-indol-3-yl)propyl]piperazine;

4-[2-(4-fluorophenyl)ethyl]-1-[2-fluoro-3-(5-(1,2,4-triazol-4-yl)-1H-indol-3-yl)propyl]piperazine;

4-[2-(3-pyridyl)propyl]-1-[2-fluoro-3-(5-(1,2,4-triazol-4-yl)-1H-indol-3-yl)propyl]piperazine;

4-[2-(4-pyridyl)propyl]-1-[2-fluoro-3-(5-(1,2,4-triazol-4-yl)-1H-indol-3-yl)propyl]piperazine;

4-[2-(2-pyridyl)propyl]-1-[2-fluoro-3-(5-(1,2,4-triazol-4-yl)-1H-indol-3-yl)propyl]piperazine;

4-[2-(3-fluorophenyl)ethyl]-1-[(S)-2-fluoro-3-(5-(1,2,4-triazol-4-yl)-1H-indol-3-yl)propyl]piperazine;

4-[2-(3-fluorophenyl)ethyl]-1-[(R)-2-fluoro-3-(5-(1,2,4-triazol-4-yl)-1H-indol-3-yl)propyl]piperazine;

4-[2-(3-fluorophenyl)ethyl]-1-[2,2-difluoro-3-(5-(1,2,4-triazol-4-yl)-1H-indol-3-yl)propyl]piperazine;

4-(2-phenylpropyl)-1-[2,2-difluoro-3-(5-(1,2,4-triazol-4-yl)-1H-indol-3-yl)propyl]piperazine;

4-[2-(4-fluorophenyl)propyl]-1-[2,2-difluoro-3-(5-(1,2,4-triazol-4-yl)-1H-indol-3-yl)propyl]piperazine;

4-[2-(2-thienyl)ethyl]-1-[2,2-difluoro-3-(5-(1,2,4-triazol-4-yl)-1H-indol-3-yl)propyl]piperazine;

4-[2-(3-thienyl)ethyl]-1-[2,2-difluoro-3-(5-(1,2,4-triazol-4-yl)-1H-indol-3-yl)propyl]piperazine;

4-[(S)-2-phenylpropyl]-1-[2,2-difluoro-3-(5-(1,2,4-triazol-4-yl)-1H-indol-3-yl)propyl]piperazine;

4-[2-(3-pyridyl)propyl]-1-[2,2-difluoro-3-(5-(1,2,4-triazol-4-yl) -1H-indol-3-yl)propyl]piperazine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein —F—G— represents —$CH_2$—N— may be prepared by a process which comprises attachment of the $R^1$ moiety to a compound of formula III:

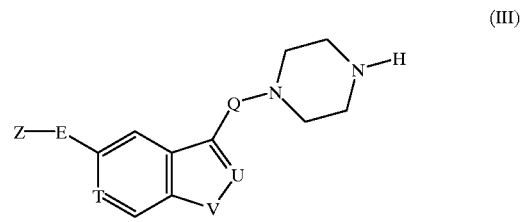

(III)

wherein Z, E, Q, T, U and V are as defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as benzyl iodide, typically under basic conditions, e.g. sodium hydride or potassium carbonate in N,N-dimethylformamide, or triethylamine in acetonitrile. Another example comprises treatment of the compound of formula III with an aryl($C_{1-6}$)alkyl or heteroaryl($C_{1-6}$)alkyl mesylate such as 2-(4-cyanophenyl)ethyl methanesulphonate or 2-(2- or 3-thienyl)ethyl methanesulphonate, typically in the presence of sodium carbonate or potassium carbonate and optionally sodium iodide, in a suitable solvent such as 1,2-dimethoxyethane or N,N-dimethylformamide.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, (3-fluorophenyl)acetaldehyde, furfuraldehyde or thiophene carboxaldehyde, in the presence of a reducing agent such as sodium cyanoborohydride. In a typical two-step procedure, for the preparation of a compound of formula I wherein $R^1$ corresponds to a group of formula —$CH_2R^{11}$, a carboxylic acid derivative of formula $R^{11}$—$CO_2H$ is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein $R^1$ represents —$COR^{11}$; the carbonyl group thereof can then be reduced, for example by treatment with diisobutylaluminium hydride, and the required compound of formula I thereby obtained.

The compounds of formula III above wherein T represents CH, U represents C—$R^2$ and V represents N—$R^3$, corresponding to the indole derivatives of formula ID as defined above wherein T represents CH, —F—G— represents —$CH_2$—N— and $R^1$ is hydrogen, may be prepared by a process which comprises reacting a compound of formula IV:

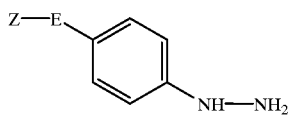
(IV)

wherein Z and E are as defined above; with a compound of formula V, or a carbonyl-protected form thereof:

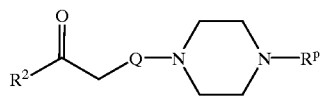
(V)

wherein $R^2$ and Q are as defined above, and $R^P$ represents an amino-protecting group; followed, where required, by N-alkylation by standard methods to introduce the moiety $R^3$; with subsequent removal of the amino-protecting group $R^P$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^P$ in the compounds of formula V is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

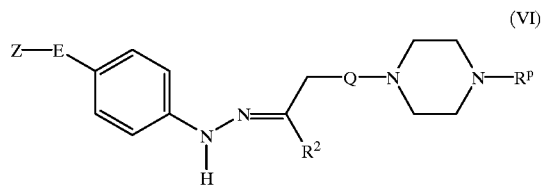
(VI)

wherein Z, E, Q, $R^2$ and $R^P$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

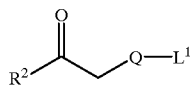
(VII)

(VIII)

wherein Q, $R^2$ and $R^P$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein T represents CH, U represents C—$R^2$ and V represents N—$R^3$—i.e. the indole derivatives of formula ID as defined above wherein T represents CH—may alternatively be prepared by a process which comprises reacting a compound of formula IV as defined above with a compound of formula IX, or a carbonyl-protected form thereof:

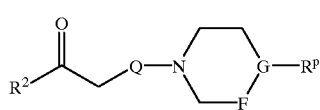
(IX)

wherein Q, F, G, $R^1$ and $R^2$ are as defined above: under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula IX include the dimethyl acetal or ketal derivatives.

As with that between compounds IV and V, the Fischer reaction between compounds IV and IX may be carried out in a single step, or may proceed via an initial non-cyclising step at a lower temperature to give an intermediate of formula X:

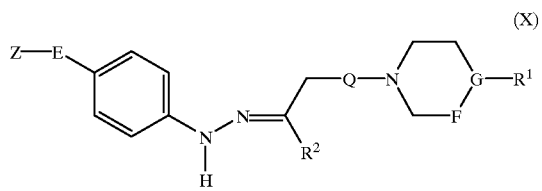
(X)

wherein Z, E, Q, F, G, $R^1$ and $R^2$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

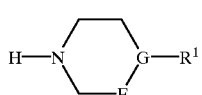
(XI)

wherein F, G and $R^1$ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

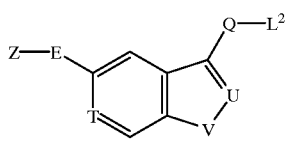

(XII)

wherein Z, E, Q, T, U and V are as defined above, and $L^2$ represents a suitable leaving group; followed by removal of the amino-protecting group $R^p$.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy), trifluoromethanesulphonyloxy (triflyloxy) or p-toluenesulphonyloxy (tosyloxy).

Where $L^2$ represents an alkylsulphonyloxv or arylsulphonvloxy group, the reaction between compound XII and compound VIII or XI is conveniently carried out in a suitable solvent such as 1,2-dimethoxyethane, isopropyl alcohol or N,N-dimethylformamide, typically in the presence of a base such as sodium carbonate or potassium carbonate, optionally with the addition of sodium iodide.

In a further procedure, the compounds of formula III above wherein T represents CH, U represents nitrogen and V represents N—$R^3$, corresponding to the indazole derivatives of formula IB as defined above wherein —F—G— represents —$CH_2$—N— and $R^1$ is hydrogen, may be prepared by a process which comprises cyclising a compound of formula XIII:

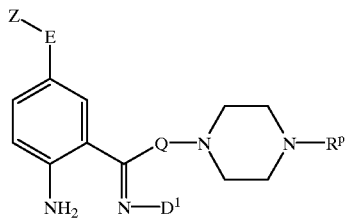

(XIII)

wherein Z, E, Q and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein T represents CH, U represents nitrogen and V represents N—$R^3$— i.e. the indazole derivatives of formula IB as defined above—may be prepared by a process which comprises cyclising a compound of formula XIV:

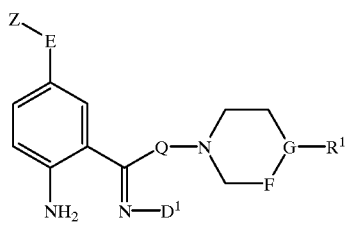

(XIV)

in which Z, E, Q, F, G, $R^1$ and $D^1$ are as defined above; followed, where required, by N-alkylation by standard methods to introduce the moiety $R^3$.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

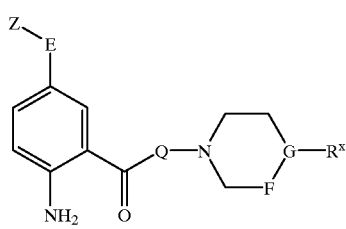

(XV)

wherein Z, E, Q, F and G are as defined above, and $R^x$ corresponds to the group $R^1$ as defined above, or $R^x$ represents an amino-protecting group as defined for $R^p$ when —F—G— represents —$CH_2$—N—; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XV may conveniently be prepared by ozonolysis of the corresponding indole derivative of formula XVI:

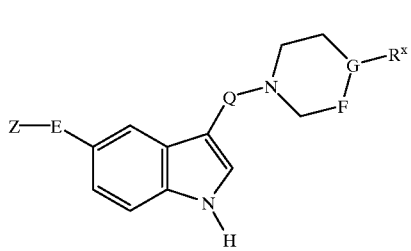

(XVI)

wherein Z, E, Q, F, G and $R^x$ are as defined above; followed by a reductive work-up, advantageously using dimethylsulphide.

The indole derivatives of formula XVI may be prepared by methods analogous to those described in the accompanying Examples, or by procedures well known from the art.

In a still further procedure, the compounds of formula III above wherein T represents CH, U represents C—R² and V represents oxygen or sulphur, corresponding to the benzofuran or benzthiophene derivatives of formula IA wherein V is oxygen or sulphur respectively, —F—G— represents —CH₂—N— and R¹ is hydrogen, may be prepared by a process which comprises cyclising a compound of formula XVII:

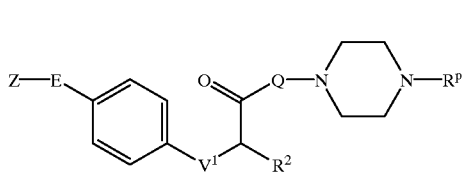

(XVII)

wherein Z, E, Q, R² and R^P are as defined above, and V¹ represents oxygen or sulphur; followed by removal of the amino-protecting group R^P.

Similarly, the compounds of formula I wherein T represents CH, U represents C—R² and V represents oxygen or sulphur—i.e. the benzofuran or benzthiophene derivatives of formula IA above—may be prepared by a process which comprises cyclising a compound of formula XVIII:

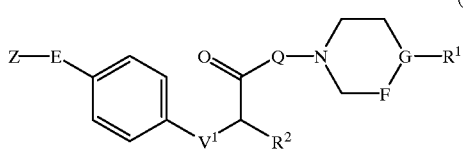

(XVIII)

wherein Z, E, Q, F, G, R¹, R² and V¹ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

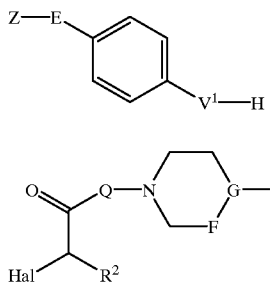

(XIX)

(XX)

wherein Z, E, Q, F, G, R², V₁ and R^x are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

In a yet further procedure, the compounds of formula III above may be prepared by a process which comprises reducing a compound of formula XXI:

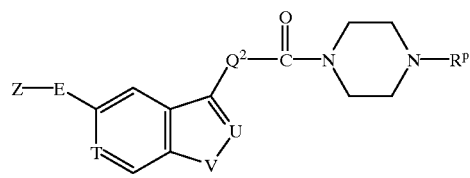

(XXI)

wherein Z, E, T, U, V and R^P are as defined above, and —Q²—CH₂— corresponds to the moiety Q as defined above; with subsequent removal of the amino-protecting group R^P.

Similarly, the compounds according to the invention may be prepared by a process which comprises reducing a compound of formula XXII:

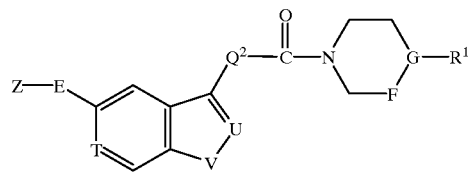

(XXII)

wherein Z, E, T, U, V, F, G, R¹ and Q² are as defined above.

The reduction of compounds XXI and XXII is conveniently effected by treating the appropriate compound with a reducing agent such as lithium aluminium hydride in an appropriate solvent, e.g. diethyl ether or tetrahydrofuran, or mixtures thereof.

The compounds of formulae XXI and XXII above may suitably be prepared by reacting a compound of formula XXIII with the appropriate compound of formula XXIV:

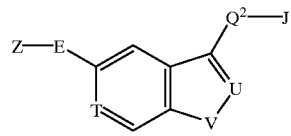

(XXIII)

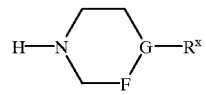

(XXIV)

wherein Z, E, T, U, V, F, G, R^x and Q² are as defined above, and J represents a reactive carboxylate moiety.

Suitable values for the reactive carboxylate moiety J include esters, for example C₁₋₄ alkyl esters; acid anhydrides, for example mixed anhydrides with C₁₋₄ alkanoic acids; acid halides, for example acid chlorides; and acylimidazoles.

By way of example, the intermediates of formula XXIII above wherein J is an acid chloride moiety may be prepared by treating the corresponding carboxylic acid derivative with thionyl chloride in toluene. Similarly, the intermediates of formula XXIII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XXIV.

In a still further procedure, the compounds of formula III above may be prepared by a process which comprises reacting a compound of formula XXV:

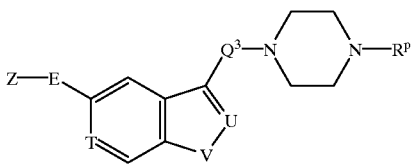

(XXV)

wherein Z, E, T, U, V and $R^p$ are as defined above, and $Q^3$ corresponds to the moiety Q as defined above in which the or each fluorine atom is replaced by a leaving group; with an available source of fluoride ion; with subsequent removal of the amino-protecting group $R^p$.

Similarly, the compounds according to the invention may be prepared by a process which comprises reacting a compound of formula XXVI:

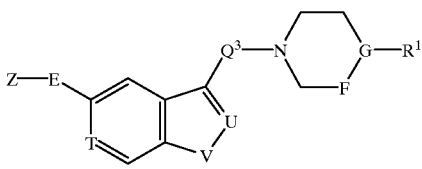

(XXVI)

wherein Z, E, T, U, V, F, G, $R^1$ and $Q^3$ are as defined above; with an available source of fluoride ion.

The source of fluoride ion for use in the above reaction with compounds XXV and XXVI is suitably tetra-n-butylammonium fluoride, in which case the reaction is conveniently carried out in a solvent such as N,N-dimethylformamide at an elevated temperature.

The leaving group present in the moiety $Q^3$ in compounds XXV or XXVI is suitably an alkylsulphonyloxy or arylsulphonyloxy group such as mesyloxy or tosyloxy, preferably mesyloxy. Where this group is mesyloxy, the appropriate compound of formula XXV or XXVI can conveniently be obtained by treatment of the corresponding hydroxy compound with mesyl chloride in the presence of triethylamine, in a solvent such as tetrahydrofuran. The required hydroxy precursor can in turn be prepared by methods analogous to those described above for the preparation of the compounds of formula III and I respectively.

The hydrazine derivatives of formula IV above may be prepared by methods analogous to those described in EP-A-0438230, EP-A-0497512, EP-A-0548813 and WO-A-91/18897.

Where they are not commercially available, the starting materials of formula VII, VIII, XI, XII, XX and XXIV may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein —F—G— represents —CH=C— initially obtained may be readily converted into the corresponding compound wherein —F—G— represents —CH$_2$—CH— by conventional catalytic hydrogenation procedures. In addition, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D_\alpha}$ receptor subtype, inhibit forskolin-stimulated adenylyl cyclase activity, and stimulate $[^{35}S]$-GTPγS binding to membranes from clonal cell lines expressing human cloned receptors.

$5\text{-HT}_{1D_\alpha}/5\text{-HT}_{1D_\beta}$ Radioligand Binding

Chinese hamster ovary (CHO) clonal cell lines expressing the human $5\text{-HT}_{1D_\alpha}$ and $5\text{-HT}_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM $[^3H]$-5-HT for saturation studies or 2–5 nM $[^3H]$-5-HT for displacement studies. The final assay volume was 1 ml. 5-HT (10 µM) was used to define non-specific binding. The reaction was initiated by the addition of membrane and was terminated by rapid filtration through Whatman GF/B filters (presoaked in 0.3% PEI/ 0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D_\alpha}$ receptor subtype obtained for the compounds of the accompanying Examples were below 50 nM in each case. Furthermore, the compounds of the accompanying Examples were all found to possess a selective affinity for the $5\text{-HT}_{1D_\alpha}$ receptor subtype of at least 10-fold relative to the $5\text{-HT}_{1D_\beta}$ subtype.

$5\text{-HT}_{1D_\alpha}/5\text{-HT}_{1D_\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D_\alpha}$ and $5\text{-HT}_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\beta\text{-}[^{33}P]$-ATP to $[^{33}P]$-cyclic AMP. A 10 µl aliquot of the membrane suspension was incubated, for 10–15 min, in a final volume of 50 µl, at 30° C., with or without forskolin (10 µM), in the presence or absence of test compound. The incubation buffer consisted of 50 mM Tris HCl (pH 7.6 at room temperature), 100 mM NaCl, 30 µM GTP, 50 µM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 µCi α-$[^{33}P]$-ATP and 1 nCi $[^3H]$-cyclic AMP. The incubation was initiated by the addition of membrane, following a 5 min preincubation at 30° C., and was terminated by the addition of 100 µl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the $5\text{-HT}_{1D_\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D_\alpha}$ receptor subtype relative to the $5\text{-HT}_{1D_\beta}$ subtype.

$5\text{-HT}_{1D_\alpha}/5\text{-HT}_{1D_\beta}$ GTPγS Binding

Studies were performed essentially as described in *Br. J. Pharmacol.*, 1993, 109, 1120. CHO clonal cell lines expressing the human cloned $5\text{-HT}_{1D_\alpha}$ and $5\text{-HT}_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 µg protein/ml for the $5\text{-HT}_{1D_\alpha}$ receptor transfected cells and 40–50 µg protein/ml for the $5\text{-HT}_{1D_\beta}$ receptor transfected cells. The membrane suspension was then incubated, in a volume of 1 ml, with GDP (100 µM for $5\text{-HT}_{1D_\alpha}$ receptor transfected cells, 30 µM for the $5\text{-HT}_{1D_\alpha}$ receptor transfected cells) and test compound at 30° C. for 20 min and then transferred to ice for a further 15 min. $[^{35}S]$-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the $5\text{-HT}_{1d_\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D_\alpha}$ receptor subtype relative to the $5\text{-HT}_{1D_\beta}$ subtype.

INTERMEDIATE 1
4-(1,2,4-Triazol-4-yl)phenylhydrazine
Prepared as described in WO 94/03446.

INTERMEDIATE 2
3-Fluorophenylacetaldehyde a) 1-(3-Fluorophenyl)-2-methoxyethene Phenyllithium (98.3 ml of a 1.8M solution in cyclohexane/diethyl ether, 177 mmol) was added to a stirred suspension of (methoxymethyl)triphenylphosphonium chloride (60.82 g, 177 mmol) (dried overnight at 50° C. in vacuo prior to use), in diethyl ether (500 ml) at 0° C. under nitrogen. The solid was seen to dissolve and a bright orange/brown coloration formed. The mixture was stirred at 0° C. for 0.25 h and then at room temperature for 0.5 h. The mixture was cooled to −20° C. and 3-fluorobenzaldehyde (20.0 g, 161 mmol) then added. The reaction mixture was allowed to warm to room temperature and stirred overnight (16 h). Saturated ammonium chloride solution (250 ml) was added and the aqueous phase separated and extracted further with diethyl ether (×2). The combined etheral layers were dried (MgSO$_4$), evaporated in vacuo and the residue distilled (≈60° C. at 1.3 mbar) to remove the majority of the phosphorous by-products. The distillate was then purified by column chromatography on silica gel, eluting with ethyl acetate/hexane (2:98) to give the title-enol ether as an E/Z mixture (10.7 g, 44%), δH (250 MHz,CDCl$_3$) 3.69 and 3.80 (total 3H, 2 of s, OCH$_3$), 5.21 and 5.77 (total 1H, 2 of d, J=7.0 Hz and 13.0 Hz respectively, C=CH$_z$ and C=CH$_E$), 6.18 (d, J=7.0 Hz, C=CH$_z$), 6.78–7.41 (m, Ar—H and C=CH$_E$).

b) 3-Fluorophenylacetaldehyde

Concentrated hydrochloric acid (45 ml) was added to a stirred solution of the preceding enol ether (7.22 g, 47.5 mmol) in THF (225 ml), at 0° C. The mixture was stirred under nitrogen for 0.3 h at 0° C., and then at room temperature for 3 h. Water was added and the volatiles were evaporated in vacuo. The residue was taken up in diethyl ether and the organic layer separated, washed with water (×2), saturated sodium bicarbonate solution (×1) and water (×1), dried (MgSO$_4$) and evaporated in vacuo to afford the title-aldehyde (5.81 g, 89%), δ$_H$ (250 MHz, CDCl$_3$) 3.71 (2H, d, J=2.2 Hz, CH$_2$), 6.93–7.39 (4H, m, Ar—H), 9.76 (1H, t, J=2.1 Hz, CHO).

INTERMEDIATE 3
(R,S)-2-Fluoro-3-[5-(1,2,4-triazol-4-yl)-1H-indol-3-yl]propan-1-ol a) (R,S)-2-Fluoro-5-hexen-1-ol To a cooled (−10° C.) and stirred mixture of hydrogen fluoride-pyridine (70% HF; 10 ml) and anhydrous dichloromethane (60 ml), in a polypropylene tube, was added dropwise via syringe neat 1,2-epoxy-5-hexene (13.8 ml) over 20 minutes, under nitrogen. After a further 20 minutes, the yellow solution was carefully poured into ice-water-concentrated ammonia (57 ml of ammonia; total volume 400 ml) and the aqueous mixture was saturated with solid sodium chloride. Products were extracted with diethyl ether (2×500 ml) and the combined ethereal solutions were washed with brine (45 ml), brine—10% aqueous sodium bicarbonate (5:1, 60 ml) then dried (MgSO$_4$) and concentrated (bath temperature 30° C.). Flash chromatography to the residual liquid (silica gel, hexane-diethyl ether, 65:35) followed by purification on alumina (activity III, dichloromethane), gave 4.4 g of the title compound as a colourless liquid; δ$_H$ (360 MHz, CDCl$_3$) 1.56–1.90 (2H, m), 2.10–2.30 (2H, m), 3.62–3.80 (2H, m), 4.48–4.70 (1H, dm, J=50 Hz ), 5.00–5.12 (2H, m), 5.75–5.88 (1H, m).

b) (R,S)-6-tert-Butyldimethylsilyloxy-5-fluoro-1-hexene

To a stirred solution of 2-fluoro-5-hexen-1-ol (4.4 g, 37.2 mmol) in anhydrous dimethylformamide (125 ml) were added imidazole (7.60 g, 111.7 mmol) and tert-butyldimethylsilyl chloride (8.42 g, 55.9 mmol), under nitrogen. After being stirred at room temperature for 7.5 hours, the mixture was diluted with diethyl ether (400 ml) and it was washed with water (150 ml), 1M hydrochloric acid (100 ml), 5% aqueous sodium bicarbonate (100 ml), brine (100 ml), then dried (MgSO$_4$) and concentrated. Flash chromatography of the residue (silica gel, petrol ether (40–60) to petrol ether (40–60)-5% diethyl ether) gave the title compound as a colourless liquid. Some impure fractions were repurified on alumina (activity III; petroleum ether (40–60)); total yield of product 6.72 g (77.7%); δ$_H$ (360 MHz, CDCl$_3$) 0.07 (6H, s), 0.90 (9H, s), 1.58–1.84 (2H, m), 2.10–2.30 (2H, m), 3.71 (2H, dd, J=22.2 and 4.7 Hz), 4.40–4.60 (1H, dm, J=49 Hz), 4.96–5.10 (2H, m), 5.75–5.88 (1H, m).

c) (R,S)-5-tert-Butyldimethylsilyloxy-4-fluoropentanal

Ozone was bubbled through a cooled (−75° C.) and stirred solution of the preceding olefin (6.7 g, 28.8 mmol) in anhydrous dichloromethane (150 ml) until a blue colour persisted (45 minutes). Oxygen was then bubbled for 10 minutes through the solution before it was kept under a nitrogen atmosphere. Anhydrous dimethyl sulfide (10 ml, 136.2 mmol) was added at −78° C. and the mixture was allowed to warm to room temperature. After 2 hours, solvents were removed under vacuum (bath temperature 32° C.) and the residue was purified by flash chromatography (silica gel, hexane-diethyl ether, 80:20) to give 5.45 g of the intermediate ozonide and 1 g of the required title product, as pale pink liquids. The ozonide (5.4 g, 19.28 mmol) in anhydrous dichloromethane (125 ml) was cooled to −78° C., under nitrogen, and anhydrous triethylamine (5.4 ml, 38.6 mmol) was added over 2 minutes. The resulting solution was allowed to warm to room temperature and stirred for 2.5 hours. The mixture was half concentrated under vacuum and directly chromatographed on silica gel (dichloromethane) to give 3.60 g of the title compound as a colourless liquid; δ$_H$ (360 MHz, CDCl$_3$) 0.07 (6H, s), 0.90 (9H, s), 1.90–2.05 (2H, m), 2.54–2.72 (2H, m), 3.73 (2H, dd, J=21.3 and 4.5 Hz), 4.40–4.62 (1H, dm, J=49.5 Hz), 9.81 (1H, dd, J=2.1 and 0.9 Hz).

d) (R,S)-2-Fluoro-3-[5-(1,2,4-triazol-4-yl)-1H-indol-3-yl]propan-1-ol

To a stirred solution of the preceding aldehyde (4.60 g, 19.6 mmol) in dioxane (170 ml) was added 4-(1,2,4-triazol-4-yl)phenylhydrazine (3.80 g, 21.1 mmol) followed by water (20 ml). After 15 minutes, 2M hydrochloric acid (11 ml) was added and the mixture was refluxed for 68 hours under nitrogen. Solvents were removed under vacuum and the residue was purified by flash chromatography (silica gel, dichloromethane-methanol, 90:10), then alumina (activity III, dichloromethane-methanol-ammonia, 95:5:0.5; then dichloromethane-methanol-ammonia, 90:10:1), to give 700 mg of the title compound as a yellow solid; δ$_H$ (360 MHz, DMSO-d$_6$) 2.98–3.10 (2H, m), 3.44–3.66 (2H, m), 4.66–4.88 (1H, dm, J=49 Hz), 4.93 (1H, t, J=5.6 Hz), 7.32 (1H, dd, J=8.5 and 1.9 Hz), 7.35 (1H, d, J=2.1 Hz), 7.50 (1H, d, J=8.5 Hz), 7.82 (1H, d, J=1.9 Hz), 9.00 (2H, s), 11.19 (1H, s); m/e (ES) 261 (M$^+$+1).

EXAMPLE 1

4-Benzyl-1-{(R,S)-2-(fluoromethyl)-3-[5-(1,2,4-triazol-4-yl)-1H-indol-3-yl]propyl}piperazine. 2.5 Hydrogen Oxalate 0.4 Hydrate a) 4-Benzyl-1-[(ethoxycarbonyl)acetyl]piperazine To a cooled (−20° C.) and stirred solution of N-benzylpiperazine (10 g, 56.7 mmol) and triethylamine (8.7 ml, 62.4 mmol) in dichloromethane (200 ml) was added ethyl malonyl chloride (8.5 ml, 66.4 mmol) over 10 minutes, under nitrogen. The mixture was allowed to warm to room temperature and it was stirred for 1 hour before water (100 ml) and diethyl ether (500 ml) were added. The organic phase was decanted off, washed with water (1×70 ml), 10% aqueous sodium bicarbonate (1×75 ml), brine (1×75 ml), then dried ($MgSO_4$) and concentrated. Flash chromatography of the residue (silica gel, ethyl acetate-ethanol, 95:5) afforded 9.53 g (58%) of the title compound as a colourless oil; $\delta_H$ (360 MHz, $CDCl_3$), 1.28 (3H, t, J=7.2 Hz), 2.48 (4H, br s), 3.45 (2H, s), 3.47 (2H, br s), 3.56 (2H, br s), 3.68 (2H, br s), 4.19 (2H, q, J=7.2 Hz), 7.24–7.36 (5H, m); m/e (ES) 291 ($M^+$+1).

b) (R,S)-4-Benzyl-1-[4-(1,3-dioxolan-2-yl)-2-(ethoxycarbonyl)-butyryl]piperazine To a stirred suspension of sodium hydride (60% dispersion in oil, 1.4 g) in anhydrous dimethylformamide (50 ml) was added dropwise, under nitrogen, a solution of 4-benzyl-1-[(ethoxycarbonyl)acetyl]piperazine (8.5 g, 29.3 mmol) in anhydrous dimethylformamide (50 ml) over 25 minutes at room temperature. After a further 30 minutes at room temperature, 2-(2-bromoethyl)-1,3-dioxolane (3.6 ml, 30.7 mmol) was added dropwise over 3 minutes and the resulting yellow solution was stirred for 24 hours. Water (400 ml) was added and products were extracted with diethyl ether (3×300 ml). The combined ethereal phases were washed with brine (1×150 ml), dried ($MgSO_4$) and concentrated. Flash chromatography of the residue (silica gel, diethyl ether-ethanol, 95:5) afforded 8 g of the title compound (70%) as a colourless oil; $\delta_H$ (360 MHz, $CDCl_3$) 1.25 (3H, t, J=7.1 Hz), 1.56–1.78 (2H, m), 2.06 (2H, q, J=7.4 Hz), 2.44 (4H, br s), 3.46–3.96 (11H, m), 4.16 (2H, q, J=7.1 Hz), 4.86 (1H, t, J=4.6 Hz), 7.24–7.36 (5H, m); m/e (ES) 391 ($M^+$+1).

c) (R,S)-4-Benzyl-1-[4-(1,3-dioxolan-2-yl)-2-(hydroxymethyl)-butyl]piperazine

To a cooled (−30° C.) and stirred solution of lithium aluminium hydride (1M in THF; 16.4 ml) in anhydrous tetrahydrofuran (30 ml) was added dropwise, via cannula, a solution of the product from the preceding step (3.2 g, 8.19 mmol) in anhydrous tetrahydrofuran (30 ml) over 14 minutes, under a nitrogen atmosphere. The resulting clear colourless solution was allowed to warm to room temperature and it was stirred for 4 hours before excess lithium aluminium hydride was destroyed by careful addition of tetrahydrofuran-water (80:20; 25 ml) (CAUTION! hydrogen evolution). The precipitated aluminium salts were filtered off, washed with tetrahydrofuran-water (80:20; 2×70 ml) and the filtrate was concentrated under vacuum. Flash chromatography of the residue (silica gel, diethyl ether-methanol, 92:8; and silica gel, dichloromethane-methanol, 93:7) afforded 1.96 g (71.5%) of the title compound as a colourless oil; $\delta_H$ (360 MHz, $CDCl_3$) 1.14–1.24 (2H, m), 1.62–1.72 (2H, m), 1.92–2.06 (1H, m), 2.20–2.90 (10H, m), 3.42–3.56 (3H, m), 3.72–4.00 (5H,m), 4.81 (1H, t, J=4.6 Hz), 7.20–7.36 (5H, m); m/e (ES) 335 ($M^+$+1).

d) 4-Benzyl-1-{(RS)-2-(hydroxymethyl)-3-[5-(1,2,4-triazol-4-yl)-1H-indol-3-yl-]propyl}piperazine. 2.25 Hydrogen Oxalate A solution of the preceding acetal (1.9 g, 5.68 mmol) and 4-(1,2,4-triazol-4-yl)phenylhydrazine (1.1 g, 6.25 mmol) in 4% aqueous sulfuric acid (80 ml) was stirred at room temperature for 20 minutes, then refluxed for 45 hours. After cooling, the mixture was basified with 30% aqueous sodium hydroxide, diluted with ethyl acetate (150 ml) and it was vigorously stirred for 1.5 hours. The organic phase was separated and the aqueous layer was extracted with ethyl acetate (3×300 ml). The combined organic solutions were washed with brine (50 ml), dried ($MgSO_4$) and concentrated. Flash chromatography of the residue (silica gel, dichloromethane-methanol-ammonia, 92:8:0.8) gave 1.2 g (49%) of the title compound free base as a white foam. The oxalate salt was prepared from absolute ethanol, mp 188–191° C. (Found: C, 55.94; H, 5.69; N, 13.28. $C_{25}H_{30}N_6O \times 2.25\ C_2H_2O_4$ requires: C, 55.96; H, 5.49; N, 13.27%). $\delta_H$ (360 MHz, DMSO-$d_6$) 2.14–2.24 (1H, m), 2.64–3.10 (12H, m), 3.39 (1H, dd, J=10.6 and 6.0 Hz), 3.45 (1H, dd, J=10.6 and 4.3 Hz), 3.77 (2H, m), 7.26–7.42 (7H, m), 7.49 (1H, d, J=8.6 Hz), 7.78 (1H, d, 1.9 Hz), 8.99 (2H, s), 11.17 (1H, s); m/e (ES) 431 ($M^+$+1).

e) 4-Benzyl-1-{(R,S)-2-(fluoromethyl)-3-[5-(1,2,4-triazol-4-yl)-1H-indol-3-yl]propyl}piperazine. 2.5 Hydrogen Oxalate. 0.4 Hydrate To a cooled (−20° C.) and stirred solution of 4-benzyl-1-{(R,S)-2-(hydroxymethyl)-3-[5-(1,2,4-triazol-4-yl)-1H-indol-3-yl]propyl}piperazine (135 mg, 0.31 mmol) and anhydrous triethylamine (89 μl, 0.64 mmol) in anhydrous tetrahydrofuran (3 ml) was added dropwise, under nitrogen, methanesulphonyl chloride (50 μl, 0.64 mmol). The resulting mixture was stirred at −20° C. to −10° C. for 1 hour 15 minutes before it was diluted with ethyl acetate (70 ml) and washed with brine (2×20 ml), then dried ($MgSO_4$) and concentrated (bath temperature 36° C.). The remaining residue was dissolved in anhydrous dimethylformamide (5 ml) and tetrabutylammonium fluoride (615 mg, 2.35 mmol) was added. The resulting solution was heated at 60–70° C. for 5 hours, under nitrogen. After cooling, water (50 ml) and saturated aqueous potassium carbonate (5 ml) were added and products were extracted with ethyl acetate (2×70 ml). The combined organic solutions were washed with brine (1×35 ml), dried ($MgSO_4$) and concentrated. Flash chromatography of the residue (silica gel, dichloromethane-methanol-ammonia, 95:5:0.5) afforded 28 mg of the title compound free base. The oxalate salt was prepared from ethanol-diethyl ether, mp 191–193° C. (Found: C, 54.14; H, 5.36; N, 12.49. $C_{25}H_{29}FN_6 \times 2.5 C_2H_2O_4 \times 0.4H_2O$ requires: C, 54.20; H, 5.28; N, 12.64%) $\delta_H$ (360 MHz, DMSO-$d_6$) 2.24–2.43 (1H, m), 2.56–3.00 (12H, m), 4.01 (2H, s), 4.28–4.54 (2H, m), 7.30–7.48 (7H, m), 7.51 (1H, d, J=8.5 Hz), 7.76 (1H, d, J=1.9 Hz), 9.00 (2H, s), 11.21 (1H, s); m/e (ES) 433 ($M^+$+1).

EXAMPLE 2

4-[2-(3-Fluorophenyl)ethyl]-1-{(R,S)-2-fluoro-3[5-(1,2,4-triazol-4-yl)-1H-indol-3-yl]propyl}pirerazine. 2.4 Hydrogen Oxalate a) Ethyl (R,S)-4,5-epoxypentanoate To a cooled (−5°) and stirred solution of ethyl pent-4-enoate (10 g, 78 mmol) in dichloromethane (200 ml) was added dropwise a solution of m-chloroperoxybenzoic acid (50–55%; 29.5 g) in dichloromethane (250 ml), over 30 minutes. The mixture was allowed to warm to room temperature overnight before it was diluted with diethyl ether (700 ml) and washed with 2N aqueous sodium hydroxide (150 ml), 10% sodium thiosulphate-10% sodium iodide-2N sodium hydroxide mixture (1:1:1, 2×80 ml) and brine (2×100 ml), then dried ($MgSO_4$) and concentrated. Flash chromatography (silica gel, dichloromethane to dichloromethane-diethyl ether, 1:1) of the residue afforded 10 g (89%) of the title compound as a colourless liquid; $\delta_H$ (360 MHz, CDCl$_3$) 1.27 (3H, t, J=7.1 Hz), 1.79 (1H, qn, J=7.0 Hz ), 1.97 (1H, m), 2.46 (2H, t, J=7.2 Hz), 2.51 (1H, m), 2.77 (1H, m), 2.99 (1H, m), 4.15 (2H, q, J=7.1 Hz).

(R,S)-γ-[(4-tert-Butyloxycarbonylpiperazin-1-yl)methyl]-butyrolactone

A solution of the preceding epoxide (6.33 g, 43.9 mmol) and 4-tert-butyloxycarbonylpiperazine (16.35 g, 87.7 mmol) in toluene (100 ml) was heated at 90° C. for 67 hours, under a nitrogen atmosphere. The solvent was removed under vacuum and the residue was dissolved in diethyl ether (500 ml) and washed with water (50 ml), brine (75 ml), then dried (Na$_2$SO$_4$) and concentrated. Flash chromatography of the residue [silica gel, diethyl ether-ethanol (90:10) to diethyl ether-methanol (90:10) to dichloromethane-methanol-ammonia (95:5:0.5)] gave 5.35 g (42.8%) of the title compound as a thick oil which solidified on standing; $\delta_H$ (250 MHz, CDCl$_3$) 1.46 (9H, s), 1.87–2.04 (1H, m), 2.25–2.38 (1H, m), 2.42–2.66 (8H, m), 3.44 (4H, t, J=5.0 Hz ), 4.62–4.74 (1H, m); m/e (ES) 285 (M$^+$+1).

c) 1-tert-Butyloxycarbonyl-4-{(R,S)-2-hydroxy-3-[5-(1,2,4-triazol-4-yl)-1H-indol-3-yl]propyl}piperazine To a cooled (–80° C.) and stirred solution of the preceding lactone (5.35 g, 18.8 mmol) in anhydrous toluene (200 ml) was added dropwise, via cannula, a solution of diisobutylaluminium hydride (1.5M in toluene, 20 ml) over 35 minutes, under nitrogen. After being stirred at –82° C. for 2 hours 20 minutes, the reaction was quenched by dropwise addition of methanol (15 ml) followed by aqueous potassium sodium tartrate (20%, 200 ml) and ethyl acetate (100 ml). The mixture was vigorously stirred while warming to room temperature and the organic phase was decanted off. The aqueous layer was extracted with ethyl acetate (3×250 ml) and the combined organic solutions were washed with brine (50 ml), then dried (MgSO$_4$) and concentrated. Flash chromatography of the residue (silica gel, diethyl ether-methanol, 90:10 to 85:15) gave 4.60 g (85.5%) of the intermediate lactol as a thick pale yellow oil; m/e (ES) 287 (M$^+$+1).

A solution of the above lactol (4.60 g, 16.1 mmol) and 4-(1,2,4-triazol-4-yl)phenylhydrazine (3.09 g, 17.7 mmol) in 4% sulfuric acid (200 ml) was stirred at room temperature for 1 hour and then refluxed for 16.5 hours, under nitrogen. After cooling, the mixture was basified with solid potassium hydroxide and products were extracted with n-butanol (2×250 ml). The combined organic solutions were concentrated under vacuum and the residue was dissolved in a mixture of tetrahydrofuran (200 ml) and isopropanol (50 ml). Di-tert-butyl dicarbonate (3.5 g, 16.1 mmol) was added and the mixture was stirred for 1 hour before it was basified (to pH 12) with 2N sodium hydroxide. Di-tert-butyl dicarbonate (1 g) was added and stirring was continued for 30 minutes before solvents were removed under vacuum. The remaining residue was diluted with water (200 ml) and extracted with hexane (2×150 ml). The aqueous layer was extracted with ethyl acetate (4×250 ml) and the combined extracts were washed with brine (100 ml), dried (MgSO$_4$) and concentrated. Flash chromatography of the residue (silica gel, dichloromethane-methanol-ammonia, 95:5:0.5; and silica gel, dichloromethane-methanol-ammonia, 92:8:0.8) afforded 1.57 g of the title compound as a yellow foam; $\delta_H$ (360 MHz, CDCl$_3$) 1.45 (9H, s), 2.32–2.48 (4H, m), 2.56–2.64 (2H, m), 2.89 (2H, d, J=5.9 Hz), 3.36–3.50 (4H, m), 4.00–4.08 (1H, m), 7.14 (1H, dd, J=5.8 and 2.1 Hz), 7.27 (1H, d, J=2.3 Hz), 7.48 (1H, d, J=8.5 Hz), 7.66 (1H, d, J=2.1 Hz), 8.47 (2H, s), 8.68 (1H, br s); m/e (ES) 427 (M$^+$+1).

d) 4-[2-(3-Fluorophenyl)ethyl]-1-{(R,S)-2-fluoro-3-[5-(1,2,4-triazol-4-yl)-1H-indol-3-yl]propyl}piperazine. 2.4 Hydrogen Oxalate To a cooled (–10° C.) and stirred solution of the preceding secondary alcohol (500 mg, 1.17 mmol) and anhydrous triethylamine (326 µl, 2.34 mmol) in anhydrous tetrahydrofuran (10 ml) was added methanesulphonyl chloride (185µl, 2.34 mmol) over 2 minutes, under nitrogen. The resulting cloudy solution was stirred at –10° C. for 0.5 hours and at room temperature for 2 hours before it was diluted with ethyl acetate (125 ml), washed with brine-water (1:1, 30 ml), brine (30 ml), dried (MgSO$_4$), and concentrated. The residual yellow foam was dissolved in anhydrous dimethylformamide (15 ml), solid tetrabutylammonium fluoride (2.70 g) was added, and the resulting solution was heated at 70° C. for 7 hours, under nitrogen. After cooling, the mixture was diluted with water (100 ml), saturated aqueous potassium carbonate (3 ml) was added, and products were extracted with ethyl acetate (2×100 ml). The combined organic phases were washed with brine (60 ml), dried (MgSO$_4$) and concentrated. Flash chromatography of the residue (silica gel, dichloromethane-methanol-ammonia, 95:5:0.5) gave 57 mg (11.4%) of 1-tert-butyloxycarbonyl-4-{(R,S)-2-fluoro-3-[5-(1,2,4-triazol-4-yl)-1H-indol-3-yl]propyl}piperazine; m/e (ES) 429 (M$^+$+1).

A solution of the above fluoro compound (55 mg, 0.128 mmol) in methanol (5 ml) and concentrated hydrochloric acid (3 ml) was allowed to stand at room temperature for 1.5 hours. Solvents were removed under vacuum and the residue was azeotroped with methanol (2×10 ml) to give a pale brown foam (60 mg). This was dissolved in methanol (4 ml) and sodium methoxide (30% w/v solution in methanol; 49 µl) was added, followed by glacial acetic acid (37 µl, 0.64 mmol). A solution of 3-fluorophenylacetaldehyde (22 mg, 0.16 mmol) in methanol (1 ml) was added followed, after 10 minutes, by sodium cyanoborohydride (15 mg). The resulting solution was stirred at room temperature for 6 hours before more 3-fluorophenylacetaldehyde (17 mg) and sodium cyanoborohydride (11 mg) were added. Stirring was continued for a further 16 hours before sodium borohydride (30 mg) was added and stirring was continued for 15 minutes. 4N Sodium hydroxide (4 ml) was then added and the methanol was removed under vacuum. The remaining residue was diluted with water (10 ml) and brine (5 ml), and products were extracted with ethyl acetate (2×40 ml). The combined organic phases were washed with brine (25 ml), dried (MgSO$_4$) and concentrated. Preparative TLC purification (silica gel, dichloromethane-methanol-ammonia, 95:5:0.5) of the residue afforded 34 mg of the title compound free base. The oxalate salt was prepared from ethanol-diethyl ether, mp 193–195° C. (Found: C, 53.65; H, 5.11; N, 12.55. C$_{25}$H$_{28}$F$_2$N$_6$×2.4C$_2$H$_2$O$_4$ requires: C, 53.69; H, 4.96; N, 12.61%). $\delta_H$ (360 MHz, DMSO-d$_6$) 2.64–3.20 (16H, m), 5.04 (1H, dm, J=50 Hz ), 7.02–7.16 (3H, m), 7.38–7.40 (3H, m), 7.51 (1H, d, 8.8 Hz), 7.83 (1H, s), 9.01 (2H, s), 11.25 (1H, s); m/e (ES) 451 (M$^+$+1).

EXAMPLE 3

4-Benzyl-1-{(R,S)-2-fluoro-3-[5-(1,2,4-triazol-4-yl)-1H-indol-3-yl]propyl}piperidine. 1.75 Hydrogen Oxalate To a stirred solution of Intermediate 3 (200 mg, 0.77 mmol) in anhydrous tetrahydrofuran (30 ml) was added anhydrous triethylamine (214 µl, 1.54 mmol) followed by methanesulphonyl chloride (121 µl, 1.54 mmol). After being stirred for 2 h 50 minutes at room temperature, under nitrogen, the mixture was diluted with ethyl acetate (125 ml), washed with brine-water (1:1, 25 ml), brine (25 ml), then dried (MgSO$_4$) and concentrated.

A mixture of the mesylate thus obtained, anhydrous potassium carbonate (128 mg) and 4-benzylpiperidine (270 μl) in isopropanol (60 ml) was refluxed, under nitrogen, for 18.5 hours. Additional 4-benzylpiperidine (3 ml) was added and refluxing was resumed for 24 hours. Solvents were removed under vacuum and the residue was partitioned between water (60 ml) and ethyl acetate (75 ml). The organic phase was washed with brine (50 ml), dried ($MgSO_4$) and concentrated. Flash chromatography of the residue (silica gel, dichloromethane-methanol, 90:10; and silica gel, dichloromethane-methanol, 92:8) afforded 173 mg (54%) of the title compound free base. The oxalate salt was prepared from ethanol-diethyl ether, mp 95–100° C. (Found: C, 59.53; H, 5.43; N, 11.99. $C_{25}H_{28}FN_5 \times 1.75C_2H_2O_4$ requires: C, 59.52; H, 5.52; N, 12.18%). $\delta_H$ (360 MHz, DMSO-$d_6$) 1.34–1.52 (2H, m), 1.64–1.80 (3H, m), 2.74–2.94 (2H, m), 3.06–3.44 (6H, m), 5.20–5.42 (1H, dm, J=47 Hz), 7.12–7.22 (3H, m), 7.24–7.40 (4H, m), 7.52 (1H, d, J=8.5 Hz), 7.84 (1H, d, J=1.9 Hz), 9.00 (2H, s), 11.33 (1H, s); m/e (ES) 418 ($M^+$+1).

EXAMPLE 4

4-[(R,S)-2-(2-Fluorophenyl),propyl]-1-{(R,S)-2-fluoro-3-[5-(1,2,4-triazol-4-yl)-1H-indol-3-yl]propyl}pipeperazine Methyl 2-fluorophenylacetate (24.2 g, 0.144 mol) in THF (75 ml) was added dropwise over 20 min to a −78° C. solution of LDA (diisopropylamine (16.0 g, 0.158 mol) and n-butyl lithium (2.5 M, 61 ml)) in THF (300 ml) and stirring was continued for 1 h. Methyl iodide (22.5 g, 0.158 mol) was added dropwise over 15 min and the reaction mixture allowed to warm to room temperature over 1 h. The solution was poured into saturated ammonium chloride solution and extracted with diethyl ether. The extract was washed with brine, dried and evaporated to yield methyl 2-(2-fluorophenyl)propanoate (26.2 g, 100%) as an oil.

Methyl 2-(2-fluorophenyl)propanoate (26.2 g, 0.144 mol) was dissolved in THF (325 ml) and LiOH (1 M, 173 ml) added. The reaction mixture was stirred at room temperature for 2.5 h, before diluting with diethyl ether and extracting with water and 1N NaOH. The aqueous layer was acidified and extracted with ethyl acetate (×2). The organic extract was washed with brine, dried and evaporated to yield 2-(2-fluorophenyl)propanoic acid (22.5 g, 100%) as an oil.

2-(2-Fluorophenyl)propanoic acid (7.7 g, 0.046 mol), 1-benzylpiperazine (8.0 g, 0.045 mol), triethylamine (4.6 g, 0.046 mol) and 1-(3-dimethylaminopropyl)-3-ethyl carbodiimide hydrochloride (9.6 g, 0.050 mol) were dissolved in dichloromethane (150 ml) and stirred at room temperature for 18 h. The solution was evaporated and the residue diluted with water and extracted with brine, dried and evaporated. Chromatography on silica gel with dichloromethane-methanol (97:3) yielded 4-benzyl-1-[2-(2-fluorophenyl)propanoyl]piperazine (5.54 g, 38%) as an oil.

Lithium aluminium hydride (1M, 34 ml) was added dropwise over 15 min to a 0° C. solution of 4-benzyl-1-[2-(2-fluorophenyl)propanoyl]piperazine (5.54 g, 0.017 mol) in THF (150 ml). The reaction mixture was stirred at 0° C. for 10 min and at room temperature for 24 h, cooled to 0° C. and quenched with water (1.6 ml), 4N NaOH (1.6 ml) and water (4.5 ml). The solid was filtered off through celite and the filtrate evaporated. Chromatography on silica gel with dichloromethane-methanol (99:1) yielded 4-benzyl-1-[2-(2-fluorophenyl)propyl]piperazine (3.17 g, 60%) as a colourless oil.

4-Benzyl-1-[2-(2-fluorophenyl)propyl]piperazine (3.17 g, 0.01 mol), ammonium formate (3.2 g, 0.05 mol) and palladium (II) hydroxide on carbon (10% w/w, 1.6 g) were mixed in methanol (200 ml) and heated under reflux for 18 h. The catalyst was filtered off through celite and the filtrate evaporated. Chromatography on silica gel with dichloromethane-methanol-880 ammonia (80:8:1) yielded 1-[2-(2-fluorophenyl)propyl]piperazine (1.64 g, 73%) as a colourless oil, $\delta_H$ (250 MHz, $CDCl_3$) 1.2 (3H, d, J 7.0, Me), 2.3–2.6 (6H, m, $CH_2$), 2.8–3.0 (4H, m, $CH_2$), 3.1–3.2 (1H, m, MeCH), 6.9–7.4 (4H, m, ArH).

The mesylate (0.577 mmol) from Example 3, 1-[2-(2-fluorophenyl)propyl]piperazine (1.0 g, 4.5 mol), potassium carbonate (0.096 g, 0.692 mmol) and sodium iodide (0.085 g, 0.577 mmol) were dissolved in isopropyl alcohol (30 ml) and heated under reflux for 66 h. The solvent was evaporated, and the residue diluted with water and extracted into ethyl acetate (×2). The extract was washed with brine, dried and evaporated. Chromatography on silica gel with dichloromethane-methanol (94:6) yielded the title compound (0.126 g, 47%) which was characterised as its oxalate salt; white crystals, mp 185–186° C. (from methanol/diethyl ether); (Found: C, 55.81; H, 5.75; N, 11.85. $C_{26}H_{30}N_6F_2 \cdot 1.75C_2H_2O_4 \cdot 0.8H_2O$ requires C, 55.66; H, 5.56; N, 13.20%); $\delta_H$ (360 MHz, $d_6$-DMSO) 1.2 (3H, d, J 7, Me), 2.7–3.1 (13H, m, $CH_2$), 3.3–3.4 (2H, m, $CH_2$), 5.0–5.2 (1H, dm, $J_{HF}$ 50, CHF), 7.0–7.4 (6H, m, ArH), 7.7 (1H, d, J 9, indole H-7), 7.8 (1H, s, indole H-4), 9.0 (2H, s, triazole-H), 11.2 (1H, br s, NH); m/z (ES) 465 ($M^+$+H).

The following Examples were made in the same way:

EXAMPLE 5

4-[(R,S)-2-(3-Fluorophenyl)-propyl]-1-{(R,S)-2-fluoro-3-[5-(1,2,4-triazol-4-yl)-1H-indol-3-yl]propyl}piperazine Oxalate salt; white crystals, mp 183–185° C. (from methanol-diethyl ether); (Found: C, 53.70; H, 5.65; N, 11.67. $C_{26}H_{30}N_6F_2 \cdot 2.0 \, C_2H_2O_4 \cdot 1.5H_2O$ requires C, 53.65; H, 5.55; N, 12.51%); $\delta_H$ (360 MHz, $d_6$-DMSO) 1.2 (3H, d, J 7, Me) 2.7–3.1 (15H, m, $CH_2$), 5.0–5.2 (1H, dm, $J_{HF}$ 50, CHF), 7.0–7.4 (6H, m, ArH), 7.5 (1H, d, J 9, indole H-7), 7.8 (1H, s, indole H-4), 9.0 (2H, s, triazole-H), 11.2 (1H, br s, NH), m/z (ES) 465 ($M^+$+H).

EXAMPLE 6

4-[(R,S)-2-(4-Fluorophenyl)propyl]-1-{(R,S)-2-fluoro-3-[5-(1,2,4-triazol-4-yl)-1 H-indol-3-yl]propyl}piperazine Oxalate salt; white crystals, mp 187–189° C. (from methanol-diethyl ether); (Found: C, 54.96; H, 5.72; N, 11.75. $C_{26}H_{30}N_6F_2 \cdot 1.75 \, C_2H_2O_4 \cdot 1.2H_2O$ requires C, 55.04; H, 5.62; N, 13.06%); $\delta_H$ (360 MHz, $d_6$-DMSO) 1.2 (3H, d, J 7, Me) 2.7–3.1 (15H, m, $CH_2$), 5.0–5.2 (1H, dm, $J_{HF}$ 45, CHF), 7.15 (2H, apparent t, J 9, ArH), 7.25–7.4 (4H, m, ArH), 7.5 (1H, d, J 9, indole H-7), 7.8 (1H, s, indole H-4), 9.0 (2H, s, triazole-H), 11.3 (1H, br s, NH), m/z (ES) 465 ($M^+$+H).

EXAMPLE 7

4-(2-Phenylethyl)-1-{(R,S)-2-fluoro-3-[5-(1,2,4-triazol-4-yl)-1H-indol-3-yl]propyl}piperazine Oxalate salt; mp 194–196° C. (from methanol-diethyl ether); (Found: C, 55.87; H, 5.92; N, 12.23. $C_{25}H_{29}N_6F_2 \cdot 2.0 \, C_2H_2O_4 \cdot 0.7H_2O$ requires C, 55.71; H, 5.55; N, 13.44%); $\delta_H$ (360 MHz, $d_6$-DMSO) 2.8–3.3 (16H, m, $CH_2$), 4.9–5.2 (1H, dm, $J_{HF}$ 50, CHF), 7.2–7.4 (7H, m, ArH), 7.5 (1H, d, J 9, indole H-7), 7.8 (1H, s, indole H-4), 9.0 (2H, s, triazole-H), 11.2 (1H, br s, NH), m/z (ES) 433 ($M^+$+H).

EXAMPLE 8

4-[(R,S)-2-Phenyloropyl]-1-{(R,S)-2-fluoro-3-[5-(1,2,4-triazol-4-yl)-1H-indol-3-yl]propyl}piperazine Oxalate salt; white crystals (from methanol-diethyl ether); (Found: C, 55.80; H, 5.86; N, 12.06. $C_{26}H_{31}N_6F_2 \cdot$ $2.0C_2H_2O_4 \cdot 1.0H_2O$ requires C, 55.86; H, 5.79; N, 13.04%); $\delta_H$ (360 MHz, $d_6$-DMSO) 1.2 (3H, d, J 7, $CH_3$) 2.7–3.2 (15H, m, $CH_2$), 5.0–5.2 (1H, dm, $J_{HF}$ 50, CHF), 7.1–7.4 (7H, m, ArH), 7.5 (1H, d, J 9, indole H-7), 7.8 (1H, s, indole H-4), 9.0 (2H, s, triazole-H), 11.2 (1H, br s, NH), m/z (ES) 447 ($M^+$+H).

EXAMPLE 9

4-[2-(2-Fluorophenyl)ethyl]-1-{(R,S)-2-fluoro-3-[5-(1,2,4-triazol-4-yl)-1H-indol-3-yl]propyl}piperazine Oxalate salt; white crystals, mp 197–210° C. (from EtOH); (Found: C, 54.68; H, 5.21; N, 13.21. $C_{26}H_{28}F_2N_6 \cdot 2C_2H_2O_4 \cdot 0.2H_2O$ requires C, 54.46; H, 5.20; N, 13.14%); $\delta_H$ (360 MHz, $d_6$-DMSO) 2.7–3.2 (16H, m, $CH_2$), 5.0–5.1 (1H, dm, $J_{HF}$ 48, CHF), 7.1 (2H, m, ArH), 7.3–7.4 (4H, m, ArH), 7.52 (1H, d, J 8.6, ArH), 7.84 (1H, d, J 1.9, ArH), 9.02 (2H, s, triazole-H), 11.27 (1H, br s, NH), m/z (ES) 451 ($M^+$+H).

EXAMPLE 10

4-[2-(4-Fluorophenyl)ethyl]-1-{(R,S)-2-fluoro-3-[5-(1,2,4-triazol-4-yl)-1H-indol-3-yl]propyl}piperazine Oxalate salt; white crystals, mp 188–190° C. (from EtOH); (Found: C, 54.22; H, 5.03; N, 12.74. $C_{25}H_{28}F_2N_6 \cdot 2C_2H_2O_4 \cdot 0.2H_2O$ requires C, 54.46 H, 5.20; N, 13.14%); $\delta_H$ (360 MHz, $d_6$-DMSO) 2.8–3.2 (16H, m, $CH_2$), 5.0–5.1 (1H, dm, $J_{HF}$ 50, CHF), 7.15 (2H, t, J 9, ArH), 7.2–7.3 (4H, m, ArH), 7.51 (1H, d, J 8.6, ArH), 7.83 (1H, d, J 1.9, ArH), 9.01 (2H, s, triazole-H), 11.26 (1H, br s, NH), m/z (ES) 451 ($M^+$+H).

EXAMPLE 11

4-[(R,S)-2-(3-Pyridyl)propyl]-1-{(R,S)-2-fluoro-3-[5-(1,2,4-triazol-4-yl)-1H-indol-3-yl]propyl}piperazine Ethyl 3-pyridylacetate (12.2 g, 73.9 mmol) in THF (30 ml) was added to LDA (81 mmol) in THF (150 ml) over 10 min at −78° C. After 1 h MeI (5.1 ml, 81 mmol) was added to the yellow suspension and the mixture brought to room temperature. $H_2O$ (300 ml) and ether (300 ml) was added, the mixture separated, and the organic layer washed with $H_2O$ and brine, dried and evaporated to give ethyl 2-(3-pyridyl)propanoate (8.3 g) as a yellow oil.

This was dissolved in THF (150 ml) and $LiAlH_4$ (1M in THF, 47 ml) added at 0° C. After 1 h $H_2O$ (1.8 ml) was added, followed by 4M NaOH (1.8 ml) and $H_2O$ (5.6 ml). After stirring for 1 h the mixture was filtered and evaporated to give 2-(3-pyridyl)propan-1-ol (6.3 g) as a yellow oil.

Methanesulfonyl chloride (2.85 ml, 36.1 mmol) was added to this alcohol (4.5 g, 32.8 mmol) and $Et_3N$ (5 ml) in THF (70 ml) at 0° C. After 1 h saturated $NaHCO_3$ was added and the mixture extracted with EtOAc (×3). The organic layers was washed with brine, dried and evaporated. $K_2CO_3$ (5 g), $^iPrOH$ (60 ml) and BOC-piperazine (12.2 g, 65.5 mmol) were added and the mixture refluxed for 24 h. After cooling, the solvent was evaporated, EtOAc (150 ml) added, and the mixture washed with $H_2O$, brine, dried, evaporated, and purified by flash chromatography, eluting with $CH_2Cl_2$:MeOH (95:5 v/v) to give 1-tert-butyloxycarbonyl-4-[(R,S)-2-(3-pyridyl)propyl]piperazine (3.51 g) as a white solid.

This was dissolved in MeOH (50 ml) and HCl gas bubbled through for 5 min. After standing for a further 15 minutes the solvent was evaporated, and the residue purified by ion exchange chromatography on DOWEX 50W×8–200 ($H^+$form) resin, washing with $H_2O$ and eluting the product with 3% $NH_3$ in $H_2O$:MeOH (1:1 v/v) to give 1-[(R,S)-2-(3-pyridyl)propyl]piperazine (1.89 g) as a light brown oil.

This was coupled to the mesylate of Example 3 to give the title compound: oxalate salt; white crystals (from ethanol-diethyl ether); (Found: C, 53.59; H, 5.46; N, 15.23. $C_{25}H_{30}N_7F \cdot 2.0C_2H_2O_4 \cdot 1.1H_2O$ requires C, 53.79; H, 5.64; N, 15.14%); $\delta_H$ (360 MHz, $d_6$-DMSO) 1.2 (3H, d, J 7, Me), 2.7–3.2 (15H, m, $CH_2$), 5.0–5.2 (1H, dm, $J_{HF}$ 50, CHF), 7.3 (3H, m, ArH), 7.5 (1H, d, J 9, indole H-7), 7.7 (1H, d, J 8, pyridine H-4), 7.8 (1H, s, indole H-4), 8.4 (1H, d, J 4, pyridine H-2), 8.5 (1H, s, pyridine H-6), 9.0 (2H, s, triazole-H), 11.2 (1H, br s, NH), m/z (ES) 448 ($M^+$+H).

EXAMPLE 12

4-[(R,S)-2-(4-Pyridyl)propyl]-1-{(R,S)-2-fluoro-3-[5-(1,2,4-triazol-4-yl)-1H-indol-3-yl]propyl}piperazine 2-(4-Pyridyl)propan-1-ol was prepared by the literature procedure (J. Indian Chem. Soc. (1966), 43, 549) and taken through as in Example 11 to give the title compound: oxalate salt; white crystals (from ethanol-diethyl ether); (Found: C, 54.05; H, 5.41; N, 14.90. $C_{25}H_{30}N_7F \cdot 2.0C_2H_2O_4 \cdot 1.1H_2O$ requires C, 53.79; H, 5.64; N, 15.14%); $\delta_H$ (360 MHz, $d_6$-DMSO) 1.2 (3H, d, J 7, Me), 2.7–3.2 (15H, m, $CH_2$), 5.0–5.2 (1H, dm, $J_{HF}$ 50, CHF), 7.3 (4H, m, ArH), 7.5 (1H, d, J 9, indole H-4), 8.5 (2H, d, J 7, pyridine H-2), 9.0 (2H, s, triazole-H), 11.2 (1H, br s, NH), m/z (ES) 448 ($M^+$+H).

EXAMPLE 13

4-[(R,S)-2-(2-Pyridyl)propyl]-1-{(R,S)-2-fluoro-3-[5-(1,2,4-triazol-4-yl)-1H-indol-3-yl]propyl}piperazine 2-(2-Pyridyl)propan-1-ol was prepared by the literature procedure (J. Indian Chem. Soc. (1966) 43, 549) and taken through as in Example 11 to give the title compound: oxalate salt; white crystals, mp 140–144° C. (from EtOH); (Found: C, 53.96; H, 5.34; N, 14.83. $C_{25}H_{30}FN_6 \cdot 2C_2H_2O_4 \cdot H_2O$ requires C, 53.95; H, 5.62; N, 15.19%); $\delta_H$ (360 MHz, $d_6$-DMSO) 1.23 (3H, d, J 6.8, Me), 2.7–3.4 (15H, m, $CH_2$ and CH), 5.0–5.1 (1H, dm, $J_{HF}$ 50, CHF), 7.2–7.4 (4H, m, ArH), 7.52 (1H, d, J 8.6, ArH), 7.76 (1H, d, J 2 and 8, ArH), 7.83 (1H, d, J, 2, ArH), 8.50–8.55 (1H, m, ArH), 9.01 (2H, s, triazole-H), 11.28 (1H, s, NH), m/z (ES) 448 ($M^+$+H).

EXAMPLE 14

4-[2-(3-Fluorophenyl)ethyl]-1-{(S)-2-fluoro-3-[5-(1,2,4-triazol-4-yl)-1H-indol-3-yl]propyl}piperazine Butyllithium (48 ml, 1.6 M) was added to triethylsilylacetylene (10.7 g, 76.4 mmol) in THF (90 ml) at −78° C. over 20 min. After 10 min $BF_3 \cdot OEt_2$ (10 ml, 82 mmol) was added, then after another 10 min (−)-benzyl-(R)-glycidyl ether (8.4 g, 51 mmol) in THF (20 ml) was added over 10 min. The mixture was stirred at −78° C. for 1 h then at 0° C. for 20 min. Saturated $NH_4Cl$ was added and the mixture extracted with EtOAc (×3). The combined organic layers were washed with $H_2O$ and brine, dried, evaporated, and purified by chromatography to give (R)-5-benzyloxy-4-hydroxy-1-triethylsilyl-1-pentyne (9.4 g, 61%).

This acetylene (7.6 g, 25 mmol), 2-iodo-4-(1,2,4-triazol-4-yl)aniline (5.6 g, 19.6 mmol), LiCl (927 mg, 19.7 mmol), $Na_2CO_3$ (8.37 g, 79 mmol), and $Ph_3P$ (1.03 g, 3.93 mmol) were stirred in DMF (200 ml) at r.t. for 2 h whilst $N_2$ gas was bubbled through the mixture. $Pd(OAc)_2$ (441 mg, 1.97 mmol) was then added, and the reaction heated at 100° C. for 20 h. The mixture was cooled, filtered and evaporated. $H_2O$ (500 ml) was added, and extracted with ethyl acetate (×5). The combined organic layers were washed with $H_2O$, brine, dried, and evaporated. A mixture of EtOH and 5M HCl (300 ml, 1:1 v/v) was added, and the solution stood at r.t. for 18 h, then poured into saturated $K_2CO_3$, and extracted with EtOAc (×3). The organic layers were washed with water and brine, dried, evaporated, and purified by flash chromatography, eluting with CH$_2$Cl$_2$:MeOH (92:8 v/v) to give (R)-3-(3-benzyloxy-2-hydroxyprop-1-yl)-5-(1,2,4-triazol-4-yl)indole (1.81 g, 26%).

This was dissolved in THF (100 ml) containing triethylamine (1.43 ml, 10.3 mmol) and cooled to −5° C. Methanesulfonyl chloride (820 μl, 10.3 mmol) was added and the mixture washed with H$_2$O and brine, dried, and evaporated. DMF (30 ml) and tetrabutylammonium fluoride (14.4 g, 52 mmol) was added and the reaction stirred at 50° C. for 16 h then diluted with H$_2$O (200 ml). The mixture was extracted with EtOAc (×3) and the combined organic layers washed with H$_2$O and brine, dried, evaporated and purified by flash chromatography, eluting with CH$_2$Cl$_2$:MeOH (90: 10 v/v) to give (S)-1-benzyloxy-2-fluoro-3-(5-[1,2,4-triazol-4-yl]-1H-indol-3-yl)propane (407 mg, 22%) as a colourless foam. Debenzylation as above gave (S)-2-fluoro-3-(5-[1,2,4-triazol-4-yl]-1H-indol-3-yl)propanol as a white solid. Comparison with the racemic material by chiral HPLC (Chiral pak AS, 15% EtOH in hexane, 1 ml/min, 40° C.) showed the compound to have 95% enantiomeric excess.

This alcohol was mesylated and coupled to 1-[2-(3-fluorophenyl)ethyl]piperazine as in Example 3 to give the title compound.

EXAMPLE 15
4-[2-(3-Fluorophenyl)ethyl]-1-{(R)-2-fluoro-3-[5-(1,2,4-triazol-4-yl)-1H-indol-3-yl]propyl}piperazine This was made in the same way as Example 14, but starting with (+)-benzyl-(S)-glycidyl ether.

EXAMPLE 16
4-[2-(3-Fluorophenyl)ethyl]-1-{2,2-difluoro-3-[5-(1,2,4-triazol-4-yl)-1H-indol-3-yl]propyl}piperazine 1.25 Hydrogen oxalate 1.0 Hydrate a) Ethyl bromodifluoroacetate (5 g, 24.6 mmol) and t-butyl piperazinecarboxylate (4.58 g) were mixed and gently heated to melt the solid. The reaction was allowed to cool. Trituration with petroleum ether (Bp 60–80° C.) gave 4-(2-bromo-2,2-difluoroacetamido)-1-(t-butoxycarbonyl) piperazine as a colourless solid. δ$_H$ (250 MHz. CDCl$_3$) 1.47 (9H, s), 3.48–3.55 (4H, m), 3.64–3.66 (4H, m).

b) A solution of allyltributyl tin (4.5 ml) and the product from above (5.0 g, 14.57 mmol) in 100 ml degassed benzene was heated to reflux under a nitrogen atmosphere in the presence of α,α'-azobisisobutyronitrile (50 mg). After 24 hours, the reaction was concentrated, and chromatographed using petroleum ether and then 20% ethyl acetate-petroleum ether as eluent. 4-(2,2-Difluoropent-4-enamido)-1-(t-butoxycarbonyl)piperazine was obtained as an oil which crystallised slowly on standing. δ$_H$ (250 MHz, CDCl$_3$) 1.47 (9H, s), 2.83–3.01 (2H, m), 3.44–3.48 (4H, m), 3.59–3.63 (2H, m), 3.67–3.71 (2H, m), 5.24 (1H, s), 5.28–5.31 (1H, d, J=7.5 Hz), 5.70–5.94 (1H, m).

c) A solution of the product from above (0.5 g, 1.7 mmol) in 20 ml anhydrous THF was treated with borane-THF complex (8.2 ml of a 1.0M solution in THF). The reaction was heated to reflux for 18 h, cooled and then concentrated. Methanol was added cautiously, the reaction reconcentrated, and methanol added again. Concentration tit uacuo gave a clear oil which was dissolved in 10 ml THF and adjusted to pH 9 using 4N sodium hydroxide. Hydrogen peroxide (30% wt solution, 1 ml) was added, and the reaction allowed to stir at room temperature for 2½ hours. The organic phase was separated and the aqueous phase was extracted with diethyl ether. The combined organic phases were washed with brine, dried (MgSO$_4$) and concentrated. Chromatography using 30% ethyl acetate-petroleum ether eluent gave 4-(2,2-difluoro-5-hydroxypentan-1-yl)-1-(t-butoxycarbonyl) piperazine as a clear oil. m/e (ES) 309 (M$^+$+1); δ$_H$ (250 MHz, CDCl$_3$) 1.45 (9H, s), 1.70–1.82 (2H, m), 1.96–2.28 (2H, m), 2.54–2.64 (4H, m), 2.70–2.81 (2H, m), 3.43–3.47 (4H, m), 3.67–3.72 (2H, m), d) A solution of the product from above (1.28 g, 4.2 mmol) and triethylamine (4 ml) in 12 ml anhydrous DMSO was treated with portions of sulphur trioxide-pyridine complex (1.3 g) using occasional cooling in an ice-water bath to moderate the exotherm. When addition was complete, the reaction was cooled in an ice-water bath, quenched with water and extracted into ethyl acetate. The organic phase was dried (MgSO$_4$), concentrated and chromatographed using 20–50% ethyl acetate-petroleum ether as eluent. 4-(2, 2-Difluoro-5-pentanal)-1-(t-butoxycarbonyl)piperazine was obtained as a clear oil. m/e (ES) 307 (M$^+$+1); δ$_H$ (250 MHz, CDCl$_3$) 1.45 (9H, s), 2.13–2.27 (2H, m), 2.34–2.40 (4H m), 2.50–2.54 (2H, m), 3.39–3.43 (4H, m), 3.49 (2H, br s), 9.81 (1H, s).

e) A solution of the product from above (1.32 g, 4.3 mmol) and 4-(1,2,4-triazol-4-yl)phenylhydrazine (0.75 g) in 4% aqueous sulphuric acid was stirred at room temperature for 20 minutes and then heated to reflux for 21¾ hours. The reaction was cooled, extracted into butanol, and the organic extracts concentrated. Chromatography using methanol-dichloromethane-ammonia (10:89:1) gave 1-{2,2-difluoro-3-[5-(1,2,4-triazol-4-yl)-1H-indol-3-yl]propyl}piperazine as a brown oil. m/e (ES) 347 (M$^+$+1); δ$_H$ (250 MHz, CDCl$_3$ +d$_4$ MeOD) 2.52–2.62 (6H, m), 2.85–2.90 (4H, m), 3.35–3.48 (2H, t, J=17.5 Hz), 7.12–7.16 (1H, m), 7.30 (1H, s), 7.49–7.52 (1H, d, J=7.5 Hz), 7.64–7.65 (1H, d, J=2.5 Hz), 8.5 (2H, s).

f) A solution of the product from above (80 mg, 0.2 mmol), acetic acid (40 μl) and 3-fluorophenyl acetaldehyde (35 mg) in 4 ml methanol was stirred for 10 minutes and then treated with sodium cyanoborohydride (15 mg). A further 8 mg of aldehyde was added, and stirring was continued for 30 minutes. The reaction was quenched with 4N sodium hydroxide, concentrated and chromatographed to give the title compound. The oxalate salt was prepared from ethanol-diethyl ether, mp. 142–145° C. (Found: C, 55.53; H, 5.66; N, 13.62. C$_{25}$H$_{27}$N$_6$F$_3$. 1.25C$_2$H$_2$O$_4$. H$_2$O requires C, 55.13; H, 5.30; N, 14.02). δ$_H$ (360 MHz, d$_6$-DMSO) 2.64–2.90 (6H, m), 2.90–2.95 (2H, m), 3.00–3.22 (6H, m), 3.36–3.50 (2H, d, J=18 Hz), 7.06–7.15 (3H, m), 7.32–7.41 (3H, m), 7.52–7.55 (1H, d, J=11 Hz), 7.82 (1H, s), 8.99 (2H, s), 11.37 (1H, s); m/e (ES) 469 (M$^+$+1).

EXAMPLE 17
4-[(±)-2-Phenylpropyl]-1-{2,2-difluoro-3-[5-(1,2,4-triazolyl-4-yl)-1H-indol-3-yl]propyl}piperazine 1.0 Hydrogen Oxalate 0.9 Hydrate 1.3 Ethanolate 2-Phenylpropionaldehyde (50 mg, 0.38 mmol) was reacted in a similar manner as described in Example 16, step f to give the title compound. mp. softens at 109° C. δ$_H$ (360 MHz, d$_6$-DMSO) (Found C, 58.33; H, 6.25; N, 12.93. C$_{26}$H$_{30}$N$_6$F$_2$. C$_2$H$_2$O$_4$. 0.9H$_2$O. 1.3C$_2$H$_5$OH requires C, 58.27; H, 6.65; N, 13.33). δ$_H$ (250 MHz, d$_4$-MeOH, free base) 1.19 (3H, d, J=6.7 Hz), 2.30–2.64 (12H, m), 2.84–2.98 (1H, m), 3.42 (2H, t, J=16.2 Hz), 7.14–7.31 (7H, m), 7.51–7.65 (1H, m), 7.83 (1H, m), 8.89 (2H, s). m/e (ES) 465 (M$^+$+1).

EXAMPLE 18

4-[(±)-2-(4-Fluorophenyl)pronyl]-1-{2,2-difluoro-3-[5-(1,2,4-triazol-4-yl)-1H-indol-3-yl]propyl}piperazine Hydrogen Oxalate 2-(4-Fluorophenyl)propionaldehyde (49 mg, 0.31 mmol) and the piperazine from Example 16, step e (110 mg, 0.31 mmol) were reacted in a similar manner as described in Example 16, step f, to give the title compound. mp. softens at 65° C. $\delta_H$ (500 MHz, d$_6$-DMSO) 1.14 (3H, d, J=6.9 Hz), 2.29–2.49 (10H, m), 2.59 (2H, t, 15 Hz), 2.91 (9H, q, J=5 Hz), 3.42 (2H, t, J=15 Hz), 7.09 (2H, t, J=5 Hz), 7.23–7.25 (2H, m), 7.30–7.32 (1H, dd, J=10 and 5 Hz), 7.36–7.37 (1H, d, J=5 Hz), 7.50–7.51 (1H, d, J=5 Hz), 7.80–7.81 (1H, d, J=5 Hz), 8.97 (2H, s), 11.31 (1H, s). m/e (ES) 483 (M$^+$+1).

EXAMPLE 19

4-[2-(2-Thienyl)ethyl]-1-{2,2-difluoro-3-[5-(1,2,4-triazol-4-yl)-1H-indol-3-yl]propyl}piperazine 1,4 Hydrogen Oxalate a) A solution of 2-(2-thienyl)ethanol (5.76 g, 45 mmol) and triethylamine (6.89 ml) in 30 ml anhydrous THF was stirred at 0° C. under a nitrogen atmosphere. Methanesulfonyl chloride was added dropwise. The reaction was stirred for 1½ h, washed with water, and the organic phase dried (MgSO$_4$) and concentrated to give the mesylate. $\delta_H$ (250 MHz, CDCl$_3$) 2.92 (3H, s), 3.27 (2H, t, J=7.5 Hz), 4.42 (2H, t, J=7.5 Hz), 6.90–698 (2H, m), 7.18–7.26 (1H, m).

b) A solution of the mesylate from above (47 mg), the piperazine from Example 16, step e (80 mg, 0.2 mmol) and potassium carbonate (32 mg) in anhydrous DMF was heated to 100° C. for 2½ hours. A further quantity of the mesylate was added after 1 hour. The reaction was partitioned between ethyl acetate and water. The organic phase was dried (MgSO$_4$), concentrated and chromatographed using methanol-dichloromethane-ammonia (5:95:1). The salt was prepared as described in Example 16, step f, to give the title compound, mp.105–107° C. (Found: C, 53.17; H, 4.77; N, 14.72. C$_{28}$H$_{26}$N$_6$SF$_2$. 1.4C$_2$H$_2$O$_4$ requires C, 53.18; H, 4.98; N, 14.42). $\delta_H$ (360 MHz, d$_6$-MeOD, free base) 2.49–2.66 (11H, m), 2.95–3.00 (2H, m), 3.11–3.12 (1H, m), 3.45 (2H, t, J=14.4 Hz), 6.84–6.85 (1H, m), 6.88–6.91 (1H, m), 7.16–7.17 (1H, m), 7.26–7.34 (2H, m), 7.52–7.55 (1H, m), 7.83 (1H, s), 8.90 (2H, s). m/e (ES) 567.

EXAMPLE 20

4-[2-(3-Thienyl)ethyl]-1-{2,2-difluoro-3-[5-(1,2,4-triazol-4-yl)-1H-indol-3-yl]propyl}piperazine 1.75 Hydrogen Oxalate 1.0 Ethanolate The title compound was prepared in a similar method as described in Example 19 using 2-(3-thienyl)ethanol, mp. 161–164° C. (Found C, 50.94; H, 5.53; N, 11.55. C$_{23}$H$_{26}$F$_2$N$_6$S. 1.75C$_2$H$_2$O$_4$. C$_2$H$_5$OH requires C, 54.94; H, 5.16; N, 15.37). $\delta_H$ (360 MHz, d$_6$-DMSO) 2.68–2.90 (6H, m) 2.92–3.00 (2H, m), 3.04–3.30 (6H, m), 3.38–3.50 (2H, m), 7.05–7.06 (1H, m), 7.30–7.38 (2H, m), 7.40–7.44 (1H, m), 7.50–7.58 (2H, m), 7.80–7.84 (1H, m), 9.00 (2H, s), 11.37 (1H, s). m/e (ES) 457 (M$^+$+1).

EXAMPLE 21

4-[(S)-2-Phenylpropyl]-1-{2,2-difluoro-3-[5-(1,2,4-triazol-4-yl)-1H-indol-3-yl]propyl}piperazine 2.1 Hydrogen Oxalate 2.0 Hydrate a) A solution of 4-(2,2-difluoropent-4-enamido)-1-(t-butoxycarbonyl)piperazine (Example 16, step b) (5.0 g, 16.4 mmol) in 10 ml dichloromethane was treated with 2 ml trifluoroacetic acid. The reaction was concentrated after 24 hours, basified to pH 9 using 4N sodium hydroxide and extracted into dichloromethane. The organic extracts were dried (MgSO$_4$) and concentrated to give 4-(2,2-difluoropent-4-enamido)piperazine as a yellow oil. $\delta_H$ (250 MHz, CDCl$_3$) 2.83–3.01 (6H, m), 3.59–3.63 (2H, t, J=10 Hz), 3.67–3.71 (2H, t, J=10 Hz), 5.23 (1H, s), 5.27–5.30 (1H, d, J=7.5 Hz), 5.79–5.95 (1H, m).

b) A solution of the product from above (1.49 g, 7.3 mmol), triethylamine (2 ml) and (S)-(+)-2-phenylpropionic acid (1.1 g, 7.3 mmol) in 10 ml anhydrous dichloromethane was stirred at 0° C. under a nitrogen atmosphere and was treated with bis(2-oxo-3-oxazolidinyl)phosphinic chloride (1.95 g, 7.7 mmol). The reaction was stirred at 0° C. for ¾ h and then at room temperature for 1 h. The reaction was washed with water, dried (MgSO$_4$), concentrated and chromatographed using 20→50% ethyl acetate-petroleum ether eluent. 4-(2,2-Difluoropent-4-enamido)-1-[(S)-2-phenylpropionamido]piperazine was obtained as a clear oil. $\delta_H$ (250 MHz, CDCl$_3$) 1.44–1.47 (3H, d, J=7.5 Hz), 2.78–2.95 (3H, m), 3.2–3.5 (4H, m), 3.52–3.70 (1H, m), 3.70–4.60 (3H, m), 5.20–5.27 (2H, m), 5.73–5.89 (1H, m), 7.21–7.36 (5H, m).

c) The bis-amide from above (1.0 g, 3 mmol) was reacted in a similar manner as described in Example 16, step c. 4-(2,2-Difluoro-5-hydroxy-pentan-1-yl)-1-[(S)-2-phenylpropyl]piperazine was obtained as a clear oil. $\delta_H$ (250 MHz, d$_6$-DMSO) 1.28–1.30 (3H, d, J=5 Hz), 1.60–1.74 (2H, m), 1.90–2.18 (2H, m), 2.4–2.7 (10H, m), 2.79 (2H, t, J=15 Hz), 3.0–3.1 (1H, m) 3.48–3.58 (2H, m), 4.64 (1H, t, J=6 Hz), 7.29–7.40 (5H, m); m/e (ES) 327 (M$^+$+1).

d) The product from above (326 mg, 1 mmol) was reacted in a similar manner as described in Example 16, step d, and was used without purification in the next step.

e) The product from above was reacted in a similar manner as described in Example 16, step e, to give the title compound. The salt was prepared as described in Example 16, step f. mp. 127–130° C. (Found: C, 52.57; H, 5.13; N, 12.15. C$_{26}$H$_{30}$N$_6$F$_2$. 2.1C$_2$H$_2$O$_4$. 2H$_2$O requires C, 52.59; H, 5.58; N, 12.18). $\delta_H$ (250 MHz, d$_4$-MeOD, free base), 1.20 (3H, d, J=2.5 Hz), 2.36–2.54 (9H, m), 2.48 (2H, t, J=10 Hz), 2.87–2.96 (2H, m), 3.34 (2H, t, J=17.5 Hz), 7.14–7.32 (7H, m), 7.51–7.54 (1H, m), 7.83 (1H, d, J=2.5 Hz), 8.88 (2H, s). m/e (ES) 465 (M$^+$+1).

EXAMPLE 22

4-[(±)-2-(3-Pyridyl)propyl]-1-{2,2-difluoro-3-[5-(1,2,4-triazol-4-yl)-1H-indol-3-yl]propyl}piperazine 3.5 Hydrogen Oxalate 0.12 Hydrate a) A solution of hexamethylene tetramine (12 g) and 5-(1,2,4-triazol-4-yl)-1H-indole (10.5 g, 57.1 mmol) in acetic acid (125 ml, 30% v/v) was heated at reflux for 3 hours. The reaction was neutralized with potassium carbonate and the water removed in vacuo. The residue was triturated with water and the solid collected to give 5-(1,2,4-triazol-4-yl)-3-(carboxaldehyde)-1H-indole as a brown solid. m/e (ES) 213 (M$^+$+1).

b) A suspension of the product from above (1.01 g, 4.8 mmol), N,N-dimethylaminopyridine (DMAP) (47 mg) and di-tert-butyldicarbonate (1.03 g) in 25 ml dichloromethane, was stirred for 8 hours. Further quantities of DMAP (50 mg) and di-tert-butyldicarbonate (200 mg) were added after 1.5 hours. The reaction was concentrated, and the solid triturated with methanol, to give 5-(1,2,4-triazol-4-yl)-3-(carboxaldehyde)-1-(tert-butoxycarbonyl)indole as a beige solid. $\delta_H$ (250 MHz, d$_6$-DMSO) 1.90 (9H, s), 7.96–8.00 (1H, m), 8.46 (1H, d, J=10 Hz), 8.54 (1H, d, J=3 Hz), 9.03 (1H, s), 9.38 (2H, s), 10.34 (1H, s). m/e (ES) 313 (M$^+$+1).

c) A suspension of activated zinc dust (85 mg) and the aldehyde from above (3.2 mg, 1 mmol) in 3 ml THF and 5 drops DMF was heated to reflux under a nitrogen atmosphere. Ethyl bromodifluoroacetate (0.14 ml, 1.1 mmol) was added. After 15 minutes, a further 0.5 eq. of ethyl bromodifluoroacetate was added, followed after 15 minutes by phenyl chlorothionoformate (0.18 ml, 1.3 mmol). The reaction was heated at reflux 1.5 hours, and partitioned between water-ethyl acetate. The combined organic phases were separated, dried (MgSO$_4$), concentrated and chromatographed using 5% methanol-dichloromethane. The partially purified product was heated to reflux in 15 ml degassed toluene with tributyl tin hydride (0.27 ml, 1 mmol) and α,α'-azobisisobutyronitrile (118 mg). After 2.5 hours, the reaction was concentrated, and chromatographed using 2→5% methanol-dichloromethane. Ethyl 2,2-difluoro-3-[5-(1,2,4-triazol-4-yl)-1-(tert-butoxycarbonyl)indol-3-yl] propanoate was obtained as a yellow oil. m/e (ES) 421 (M$^+$+1). δ$_H$ (250 MHz. CDCl$_3$) 0.92 (3H, t, J=7.5 Hz), 1.69 (9H, s), 3.49 (2H, t, J=15 Hz), 4.28 (2H, q, J=7.5 Hz), 7.30–7.35 (1H, m), 7.56 (1H, m), 7.67 (1H, s), 8.30–8.34 (1H, m), 8.50 (2H, s).

d) A solution of the product from above (179 mg, 0.4 mmol) in 3 ml ethanol was treated with sodium borohydride (20 mg), and the reaction monitored by tlc. When all the starting material had reacted, the reaction was quenched by addition of water. The ethanol was removed in vacuo, and the products extracted with ethyl acetate. The organic phase was dried (MgSO$_4$), concentrated and chromatographed using 5% methanol-dichloromethane as eluent. 2,2-Difluoro-3-[5-(1,2,4-triazol-4-yl)-1-(tert-butoxycarbonyl) indol-3-yl]propan-1-ol was obtained as a yellow oil. m/e 379 (ES) (M$^+$+1). δ$_H$ (250 MHz, CDCl$_3$) 1.69 (9H, s), 3.42 (2H, t, J=17.5 Hz) 3.77 (2H, t, J=12.5 Hz), 7.30–7.34 (1H, m), 7.69 (1H, s), 7.74 (1H, s), 8.29–8.32 (1H, m), 8.60 (2H, br s).

e) A solution of the product from above (80 mg, 0.21 mmol) in 10 ml anhydrous dichloromethane and pyridine (70 μl) was cooled to an internal temperature of –50° C. under a nitrogen atmosphere. Trifluoromethanesulfonic anhydride (71 μl) was added, and the reaction allowed to stir at –25→–50° C. for 1.5 h. Five ml of water was added, and the reaction allowed to attain room temperature. The organic phase was separated, dried (MgSO$_4$), and concentrated. The crude triflate was dissolved in 3 ml anhydrous DMF and heated at 120° C. for 10 minutes with potassium carbonate (58 mg) and 1-[2-(3-pyridyl)propyl]piperazine (92 mg, 0.45 mmol). The reaction was partitioned between ethyl acetate and water. The organic phase was separated, dried (MgSO$_4$), and concentrated, and chromatographed using dichloromethane-methanol-ammonia (90:10:1) to give the title compound. (Found C, 49.01; H, 5.13; N, 12.51. C$_{25}$H$_{29}$F$_2$N$_7$. 3½C$_2$H$_2$O$_4$. ⅛H$_2$O requires C, 58.37; H, 5.62; N, 17.65. δ$_H$ (250 MHz, d$_6$-DMSO) 1.25–1.28 (3H, m), 2.35–2.62 (12H, m), 2.9–3.0 (1H, m), 3.41 (2H, t, J=17.5 Hz), 7.14–7.36 (3H, m), 7.47–7.50 (2H, m), 7.68 (1H s), 8.47 (4H, m).

We claim:

1. A compound of formula I, or a salt or prodrug thereof:

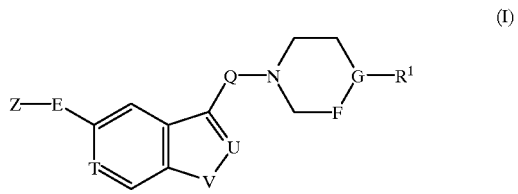

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

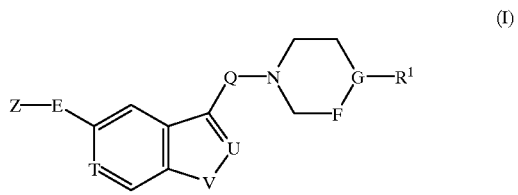

(I)

in which the asterisk * denotes a chiral center; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, substituted in any position by one or more fluorine atoms;

T represents CH;

U represents C—R$^2$;

V represents N—R$^3$;

—F—G— represents —CH$_2$—N—;

R$^1$ represents C$_{3-6}$ alkenyl, C$_{3-6}$ alkynyl, aryl(C$_{1-6}$)alkyl or heteroaryl(C$_{1-6}$)alkyl, any of which groups may be optionally substituted;

R$^2$, R$^3$ and R$^4$ independently represent hydrogen or C$_{1-6}$ alkyl; and

R$^5$ and R$^6$ independently represent hydrogen, C$_{1-6}$ alkyl, trifluoromethyl, phenyl, methylphenyl, or an optionally substituted aryl(C$_{1-6}$)alkyl or heteroaryl(C$_{1-6}$)alkyl group; or R$^5$ and R$^6$, when linked through a nitrogen atom, together represent the residue of an optionally substituted azetidine, pyrrolidine, piperidine, morpholine or piperazine ring.

2. A compound as claimed in claim 1 wherein Q represents 2-fluoropropylene, 2,2-difluoropropylene or 2-fluoromethyl-propylene.

3. A compound as claimed in claim 1 represented by formula IIA, and salts and prodrugs thereof:

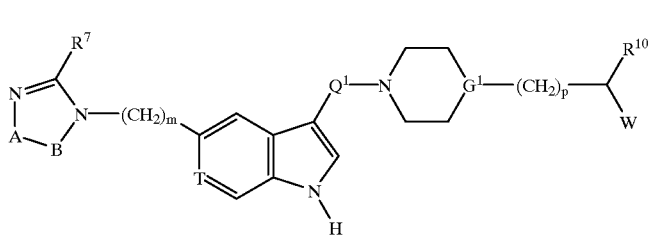

(IIA)

wherein m is zero, 1, 2 or 3;

p is zero, 1 or 2;

$Q^1$ represents a straight or branched alkylene chain containing from 2 to 5 carbon atoms, substituted in any position by one or more fluorine atoms;

T represents CH;

$G^1$ represents nitrogen;

A represents nitrogen or CH;

B represents nitrogen or C—$R^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

W represents a group of formula (Wa), (Wb) or (Wc):

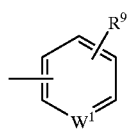
(Wa)

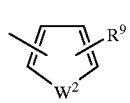
(Wb)

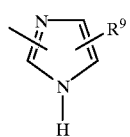
(Wc)

in which $W^1$ represents CH or nitrogen;

$W^2$ represents oxygen, sulphur, NH or N-methyl;

$R^9$ represents hydrogen, halogen, cyano, trifluoromethyl, triazolyl, tetrazolyl, $C_{1-6}$ alkyltetrazolyl, $C_{1-6}$ alkoxy, $C_{2-6}$ alkylcarbonyl, amino, $C_{1-6}$ alkylamino, di($C_{1-6}$)alkylamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and $R^{10}$ represents hydrogen or $C_{1-3}$ alkyl.

4. A compound as claimed in claim 1 represented by formula IIB, and salts and prodrugs thereof:

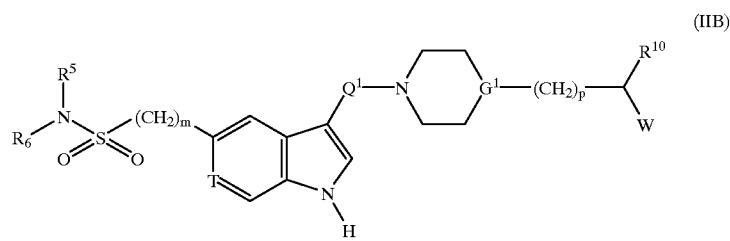

(IIB)

wherein m is zero, 1, 2 or 3;

p is zero, 1 or 2;

$Q^1$ represents a straight or branched alkylene chain containing from 2 to 5 carbon atoms, substituted in any position by one or more fluorine atoms;

T represents CH;

$G^1$ represents nitrogen;

W represents a group of formula (Wa), (Wb) or (Wc):

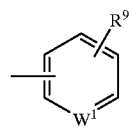
(Wa)

(Wb)

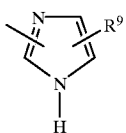
(Wc)

in which
W¹ represents CH or nitrogen;
W² represents oxygen, sulphur, NH or N-methyl;
$R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring;
$R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and
$R^{10}$ represents hydrogen or $C_{1-3}$ alkyl.

5. A compound as claimed in claim 1 represented by formula IIC, and salts and prodrugs thereof:

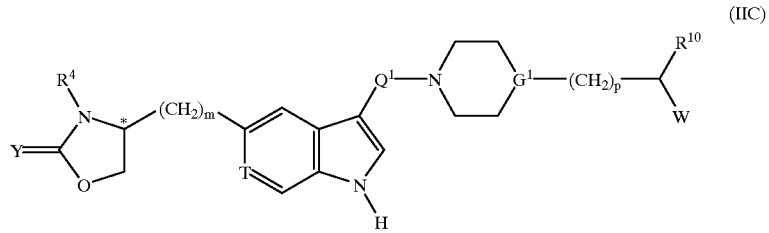
(IIC)

wherein the asterisk * denotes a chiral center;

m is zero, 1, 2 or 3;

p is zero, 1 or 2;

Y represents oxygen or sulphur;

$Q^1$ represents a straight or branched alkylene chain containing from 2 to 5 carbon atoms, substituted in any position by one or more fluorine atoms;

$R^4$ represents hydrogen or $C_{1-6}$ alkyl;

T represents CH;

$G^1$ represents nitrogen;

W represents a group of formula (Wa), (Wb) or (Wc):

(Wa)

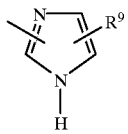
(Wb)

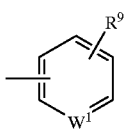
(Wc)

in which
W¹ represents CH or nitrogen;
W² represents oxygen, sulphur, NH or N-methyl;
$R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamnino, di($C_{1-6}$)alkylamino, di($C_{1-6}$)alkylaminomethyl, $C_{2-6}$ alkylcarbonylarnino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and
$R^{10}$ represents hydrogen or $C_{1-3}$ alkyl.

6. A compound selected from:
4-benzyl-1-[2-fluoromethyl-3-(5-(1,2,4-triazol-4-yl)-1H-indol-3-yl)propyl]piperazine;
4-[2-(3-fluorophenyl)ethyl]-1-[2-fluoro-3-(5-(1,2,4-triazol-4-yl)-1H-indol-3-yl)propyl]piperazine;
4-benzyl-1-[2-fluoro-3-(5-(1,2,4-triazol-4-yl)-1H-indol-3-yl)propyl]piperidine;

and salts and prodrugs thereof.

7. A compound selected from:
4-[2-(2-fluorophenyl)propyl]-1-[2-fluoro-3-(5-(1,2,4-triazol-4-yl)-1H-indol-3-yl)propyl]piperazine;
4-[2-(3-fluorophenyl)propyl]-1-[2-fluoro-3-(5-(1,2,4-triazol-4-yl)-1H-indol-3-yl)propyl]piperazine;
4-[2-(4-fluorophenyl)propyl]-1-[2-fluoro-3-(5-(1,2,4-triazol-4-yl) -1H-indol-3-yl)propyl]piperazine;
4-(2-phenylethyl)-1-[2-fluoro-3-(5-(1,2,4-triazol-4-yl)-1H-indol-3-yl)propyl]piperazine;
4-(2-phenylpropyl)-1-[2-fluoro-3-(5-(1,2,4-triazol-4-yl)-1H-indol-3-yl)propyl]piperazine;
4-[2-(2-fluorophenyl)ethyl]-1-[2-fluoro-3-(5-(1,2,4-triazol-4-yl)-1H-indol-3-yl)propyl]piperazine;
4-[2-(4-fluorophenyl)ethyl]-1-[2-fluoro-3-(5-(1,2,4-triazol-4-yl)-1H-indol-3-yl)propyl]piperazine;
4-[2-(3-pyridyl)propyl]-1-[2-fluoro-3-(5-(1,2,4-triazol-4-yl)-1H-indol-3-yl)propyl]piperazine;
4-[2-(4-pyridyl)propyl]-1-[2-fluoro-3-(5-(1,2,4-triazol-4-yl)-1H-indol3-yl)propyl]piperazine;
4-[2-(2-pyridyl)propyl]-1-[2-fluoro-3-(5-(1,2,4-triazol-4-yl)-1H-indol-3-yl)propyl]piperazine;

4-[2-(3-fluorophenyl)ethyl]-1-[(S)-2-fluoro-3-(5-(1,2,4-triazol-4-yl)-1H-indol-3-yl)propyl]piperazine;
4-[2-(3-fluorophenyl)ethyl]-1-[(R)-2-fluoro-3-(5-(1,2,4-triazol-4-yl)-1H-indol-3-yl)propyl]piperazine;
4-[2-(3-fluorophenyl)ethyl]-1-[2,2-difluoro-3-(5-(1,2,4-triazol-4-yl)-1H-indol-3-yl)propyl]piperazine;
4-(2-phenylpropyl)-1-[2,2-difluoro-3-(5-(1,2,4-triazol-4-yl)-1H-indol-3-yl)propyl]piperazine;
4-[2-(4-fluorophenyl)propyl]-1-[2,2-difluoro-3-(5-(1,2,4-triazol-4-yl)-1H-indol-3-yl)propyl]piperazine;
4-[2-(2-thienyl)ethyl]-1-[2,2-difluoro-3-(5-(1,2,4-triazol-4-yl)-1H-indol-3-yl)propyl]piperazine;
4-[2-(3-thienyl)ethyl]-1-[2,2-difluoro-3-(5-(1,2,4-triazol-4-yl)-1H-indol-3-yl)propyl]piperazine;
4-[(S)-2-phenylpropyl]-1-[2,2-difluoro-3-(5-(1,2,4-triazol-4-yl)-1H-indol-3-yl)propyl]piperazine;
4-[2-(3-pyridyl)propyl]-1-[2,2-difluoro-3-(5-(1,2,4-triazol-4-yl) -1H-indol-3-yl)propyl]piperazine;
and salts and prodrugs thereof.

8. A pharmaceutical composition comprising a compound of formula I as defined in claim 1 or a pharmaceutically acceptable salt thereof or a prodrug thereof in association with a pharmaceutically acceptable carrier.

9. A process for the preparation of a compound as claimed in claim 1, which comprises:

(A) attachment of the $R^1$ moiety to a compound of formula III:

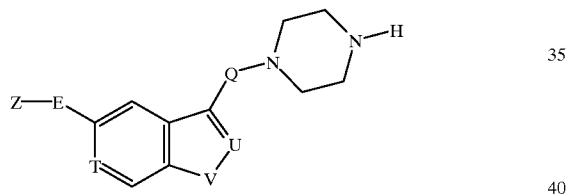

(III)

wherein Z, E, Q, T, U and V are as defined in claim 1; or (B) reacting a compound of formula IV:

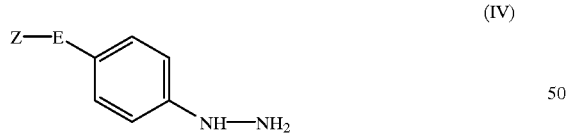

(IV)

wherein Z and E are as defined in claim 1; with a compound of formula IX, or a carbonyl-protected form thereof:

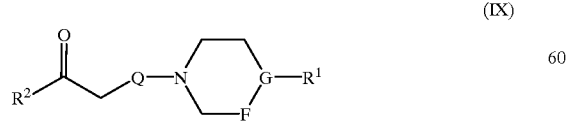

(IX)

wherein Q, F, G, $R^1$ and $R^2$ are as defined in claim 1; followed, where required, by N-alkylation by standard methods to introduce the moiety $R^3$; or (C) reacting a compound of formula XI:

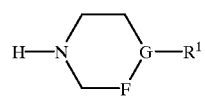

(XI)

wherein F, G and $R^1$ are as defined in claim 1; with a compound of formula XII:

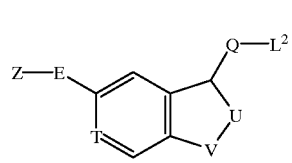

(XII)

wherein Z, E, Q, T, U and V are as defined in claim 1, and $L^2$ represents a suitable leaving group; or (D) cyclising a compound of formula XIV:

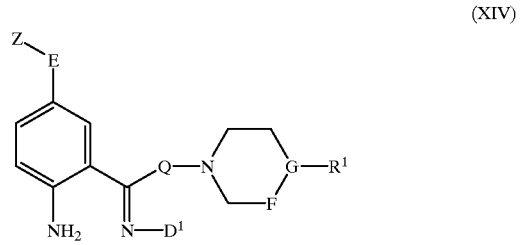

(XIV)

in which Z, E, Q, F, G and $R^1$ are as defined in claim 1, and $D^1$ represents a readily displaceable group; followed, where required, by N-alkylation by standard methods to introduce the moiety $R^3$; or (E) cyclising a compound of formula XVIII:

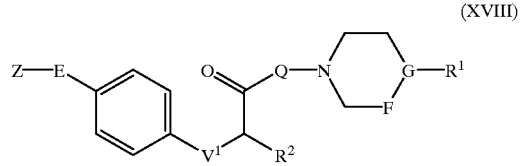

(XVIII)

wherein Z, E, Q, F, G, $R^1$ and $R^2$ are as defined in claim 1, and $V^1$ represents oxygen or sulphur; or (F) reducing a compound of formula XXII:

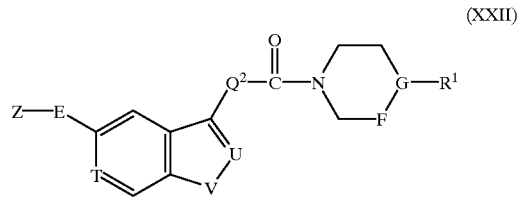

(XXII)

wherein Z, E, T, U, V, F, G and $R^1$ are as defined in claim 1, and —$Q^2$—$CH_2$— corresponds to the moiety Q as defined in claim 1; or (G) reacting a compound of formula XXVI:

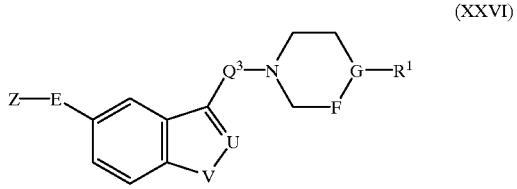

(XXVI)

wherein Z, E, T, U, V, F, G and R$^1$ are as defined in claim 1, and Q$^3$ corresponds to the moiety Q as defined in claim 1 in which the or each fluorine atom is replaced by a leaving group; with an available source of fluoride ion; and (H) subsequently, if necessary, converting a compound of formula I initially obtained into a further compound of formula I by standard methods.

10. A method for the treatment and/or prevention of clinical conditions for which an agonist of 5-HT$_{1D}$ receptors selective for the 5-HT$_{1D_\alpha}$ subtype thereof is indicated, which method comprises administering to a patient in need of such treatment an effective amount of a compound of formula I as defined in claim 1 or a pharmaceutically acceptable salt thereof or a prodrug thereof.

* * * * *